United States Patent [19]

Plyley et al.

[11] Patent Number: 5,680,983

[45] Date of Patent: *Oct. 28, 1997

[54] SAFETY DEVICE FOR A SURGICAL STAPLER CARTRIDGE

[75] Inventors: Alan K. Plyley, Santa Barbara, Calif.; Floyd L. Foslien, Hudson, Wis.; John M. Barker, Ventura, Calif.; Robert W. Petrich, Woodbury, Minn.

[73] Assignee: United States Surgical Corporation, Norwalk, Conn.

[*] Notice: The portion of the term of this patent subsequent to Jul. 5, 2014, has been disclaimed.

[21] Appl. No.: 470,262

[22] Filed: Jun. 6, 1995

Related U.S. Application Data

[63] Continuation of Ser. No. 270,397, Jul. 5, 1994, Pat. No. 5,445,304, which is a continuation of Ser. No. 629,597, Dec. 18, 1990, abandoned.

[51] Int. Cl.⁶ ............................................. A61B 17/072
[52] U.S. Cl. .......................... 227/175.3; 227/180.1; 227/178.1; 227/19
[58] Field of Search ................. 227/175.1, 175.2, 227/175.3, 175.4, 176.1, 178.1, 180.1, 8, 19

[56] References Cited

U.S. PATENT DOCUMENTS

| | | |
|---|---|---|
| D. 283,733 | 5/1986 | Rawson et al. . |
| D. 322,143 | 12/1991 | Spreckelmeier . |
| 2,174,219 | 9/1939 | Balma . |
| 2,246,647 | 6/1941 | Vancura . |
| 3,079,606 | 3/1963 | Bobrov et al. . |
| 3,490,675 | 1/1970 | Green et al. . |
| 3,494,533 | 2/1970 | Green et al. . |

(List continued on next page.)

FOREIGN PATENT DOCUMENTS

| | | |
|---|---|---|
| A-54764/86 | of 0000 | Australia . |
| A-54765 | of 0000 | Australia . |
| 0373762 | 6/1989 | European Pat. Off. . |
| 0324638 | 7/1989 | European Pat. Off. . |
| 0380025 | 8/1990 | European Pat. Off. . |
| 0489436 | 6/1992 | European Pat. Off. . |
| 7037682 | 6/1972 | France . |
| 2744824 | 2/1980 | Germany . |
| 2070499 | 9/1981 | United Kingdom . |
| 8302247 | 7/1983 | WIPO . |

OTHER PUBLICATIONS

U.S. Patent Application No. 07/629,597.
Flickinger et al., Surgical Stapling Gastric and Small Bowel Procedures, pp. 1–14.
Anderson et al., Surgical Stapling Toraci, Vascular and Esophageal Procedure, pp. 1–101.

(List continued on next page.)

Primary Examiner—Rinaldi I. Rada
Assistant Examiner—Boyer Ashley

[57] ABSTRACT

The present invention provides a staple cartridge assembly adapted for use in a surgical stapler having a cartridge retention portion and an anvil portion which are movable between a closed position and an open position. The cartridge assembly comprises (1) a firing assembly for firing staples which is movable between a pre-fired and a fired position, (2) a safety member, (3) means mounting the safety member on the cartridge assembly for movement between a free-movement position which affords movement of the cartridge retention portion and the anvil portion between the open and closed position and a blocking position which prevents the cartridge retention portion and the anvil portion from being moved to the closed position, and (4) means for releasably retaining the safety member in the free-movement position and for releasing the safety member to afford movement of the safety member toward the blocking position when the firing assembly is moved from the pre-fired to the fired position such that upon movement of the cartridge retention portion and anvil portion to the open position, the safety member prevents the cartridge portion and the anvil portion from thereafter being moved to the closed position while the stapler is loaded with the spent cartridge.

22 Claims, 9 Drawing Sheets

U.S. PATENT DOCUMENTS

| | | |
|---|---|---|
| 3,499,591 | 3/1970 | Green . |
| 3,675,688 | 7/1972 | Bryan et al. . |
| 3,692,224 | 9/1972 | Astafiev et al. . |
| 3,735,762 | 5/1973 | Bryan et al. . |
| 3,795,034 | 3/1974 | Strekopytov et al. . |
| 3,844,289 | 10/1974 | Noiles . |
| 3,873,016 | 3/1975 | Fishbein . |
| 4,006,786 | 2/1977 | Speicher . |
| 4,086,926 | 5/1978 | Green et al. . |
| 4,108,306 | 8/1978 | Samuels et al. . |
| 4,202,479 | 5/1980 | Razgulov et al. . |
| 4,202,480 | 5/1980 | Annett . |
| 4,256,251 | 3/1981 | Moshofsky . |
| 4,296,881 | 10/1981 | Lee . |
| 4,304,236 | 12/1981 | Conta et al. . |
| 4,305,539 | 12/1981 | Korolkov et al. . |
| 4,319,576 | 3/1982 | Rothfuss . |
| 4,331,276 | 5/1982 | Bourque . |
| 4,349,028 | 9/1982 | Green . |
| 4,354,628 | 10/1982 | Green . |
| 4,383,634 | 5/1983 | Green . |
| 4,391,401 | 7/1983 | Moshofsky . |
| 4,415,112 | 11/1983 | Green . |
| 4,429,695 | 2/1984 | Green . |
| 4,442,964 | 4/1984 | Becht . |
| 4,473,077 | 9/1984 | Noiles et al. . |
| 4,480,640 | 11/1984 | Becht . |
| 4,500,025 | 2/1985 | Skwor . |
| 4,506,670 | 3/1985 | Crossley . |
| 4,508,253 | 4/1985 | Green . |
| 4,519,532 | 5/1985 | Foslien . |
| 4,520,817 | 6/1985 | Green . |
| 4,523,695 | 6/1985 | Braun et al. . |
| 4,527,724 | 7/1985 | Chow et al. . |
| 4,530,453 | 7/1985 | Green . |
| 4,540,110 | 9/1985 | Bent et al. . |
| 4,556,058 | 12/1985 | Green . |
| 4,568,009 | 2/1986 | Green . |
| 4,569,346 | 2/1986 | Poirier . |
| 4,576,165 | 3/1986 | Green et al. . |
| 4,576,167 | 3/1986 | Noiles . |
| 4,589,582 | 5/1986 | Biolotti . |
| 4,591,085 | 5/1986 | DiGiovanni . |
| 4,592,498 | 6/1986 | Braun et al. . |
| 4,597,517 | 7/1986 | Wagdy . |
| 4,605,004 | 8/1986 | DiGiovanni et al. . |
| 4,606,344 | 8/1986 | DiGiovanni . |
| 4,606,345 | 8/1986 | Dorband et al. . |
| 4,607,636 | 8/1986 | Kula et al. . |
| 4,608,981 | 9/1986 | Rothfuss et al. . |
| 4,612,933 | 9/1986 | Brinkerhoff et al. . |
| 4,617,928 | 10/1986 | Alfranca . |
| 4,633,861 | 1/1987 | Chow et al. . |
| 4,633,874 | 1/1987 | Chow et al. . |
| 4,646,745 | 3/1987 | Noiles . |
| 4,664,305 | 5/1987 | Blake, III et al. . |
| 4,665,916 | 5/1987 | Green . |
| 4,684,051 | 8/1987 | Akopov et al. . |
| 4,714,187 | 12/1987 | Green . |
| 4,715,520 | 12/1987 | Roehr, Jr. et al. . |
| 4,728,020 | 3/1988 | Green et al. . |
| 4,741,336 | 5/1988 | Failla et al. . |
| 4,807,628 | 2/1989 | Peters et al. . |
| 4,809,898 | 3/1989 | Gassner et al. . |
| 4,850,355 | 7/1989 | Brooks et al. . |
| 4,863,088 | 9/1989 | Redmond et al. . |
| 4,869,415 | 9/1989 | Fox . |
| 4,881,544 | 11/1989 | Green et al. . |
| 4,881,545 | 11/1989 | Isaacs et al. . |
| 4,892,244 | 1/1990 | Fox et al. . |
| 4,915,100 | 4/1990 | Green . |
| 4,938,408 | 7/1990 | Bedi et al. . |
| 4,941,623 | 7/1990 | Pruitt . |
| 4,955,959 | 9/1990 | Tompkins . |
| 5,031,814 | 7/1991 | Tompkins . |
| 5,038,695 | 8/1991 | Foslien et al. . |
| 5,040,715 | 8/1991 | Green et al. . |
| 5,065,929 | 11/1991 | Schulze et al. . |
| 5,071,052 | 12/1991 | Rodak et al. . |
| 5,074,454 | 12/1991 | Peters . |
| 5,100,042 | 3/1992 | Gravener et al. . |
| 5,106,008 | 4/1992 | Tompkins et al. . |
| 5,129,570 | 7/1992 | Schulze et al. . |
| 5,445,304 | 8/1995 | Plyley et al. ............................ 227/176 |

OTHER PUBLICATIONS

Brolin et al., Surgical Stapling Bariatric Procedures for Morbid Obesity, pp. 1–115.

"Disposable EEA Surgical Stapler and Curved Disposable EEA Surgical Stapler", Information Booklet, printed Jan. 1985.

"Auto Suture® Premium Poly CS™–57 Disposable Surgical Stapler," printed 1986, reprinted 1990.

"Auto Suture® Poly CS™–57 Disposable Surgical Stapler," printed Jul. 1988.

"Auto Suture® Poly CS™–57 Disposable Loading Units with LACTOMER® Absorbable Copolymer Staples", printed Jul. 1988.

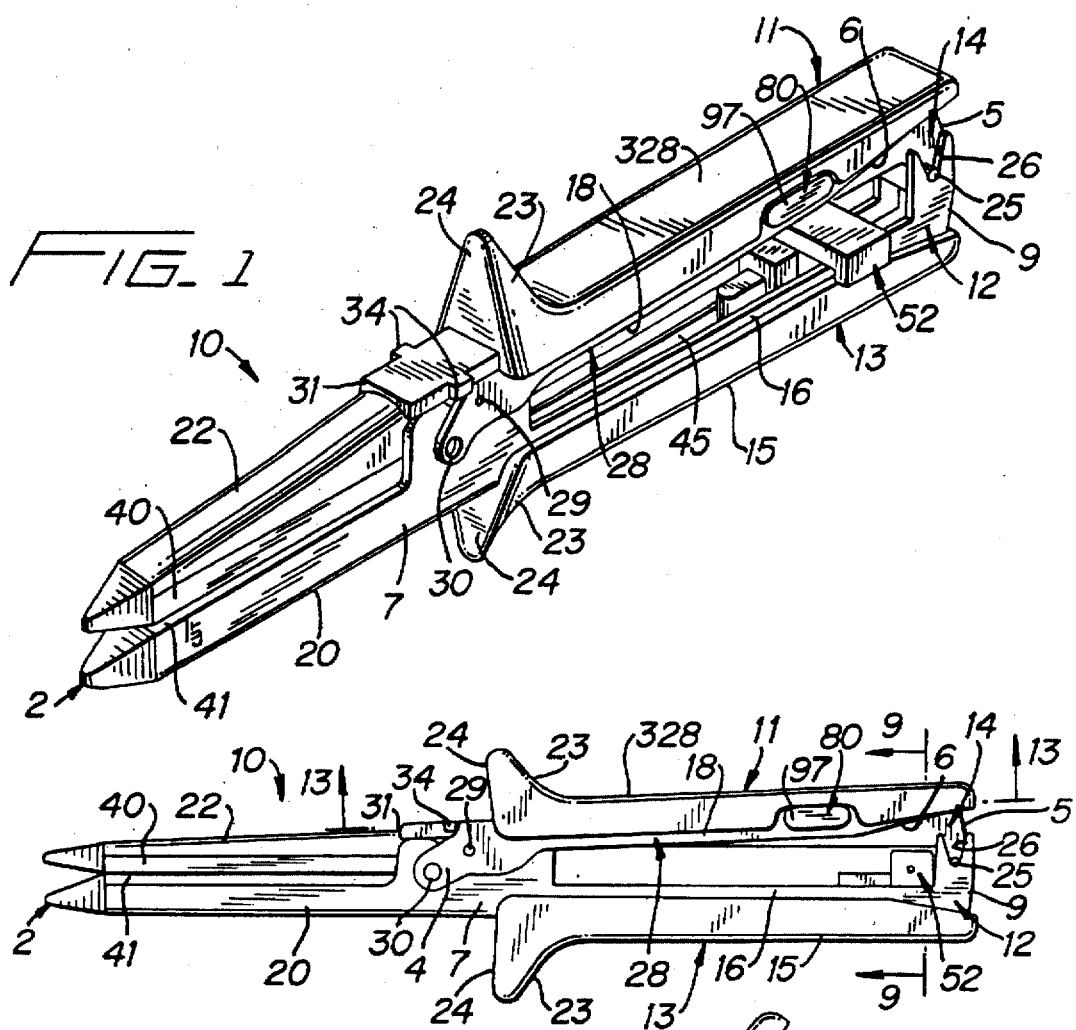
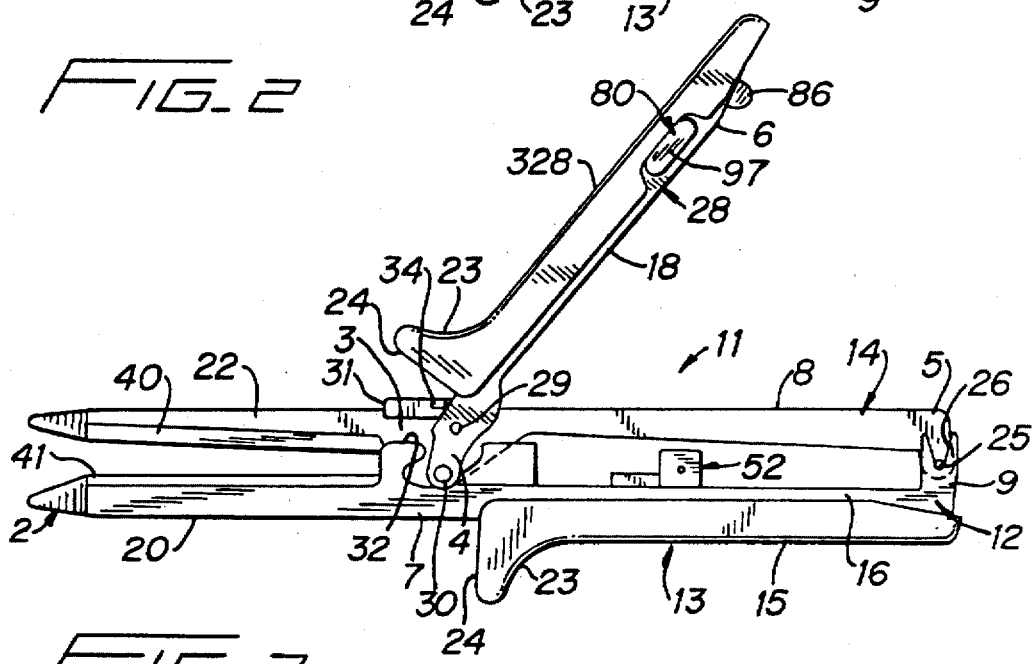

FIG_4

FIG_5

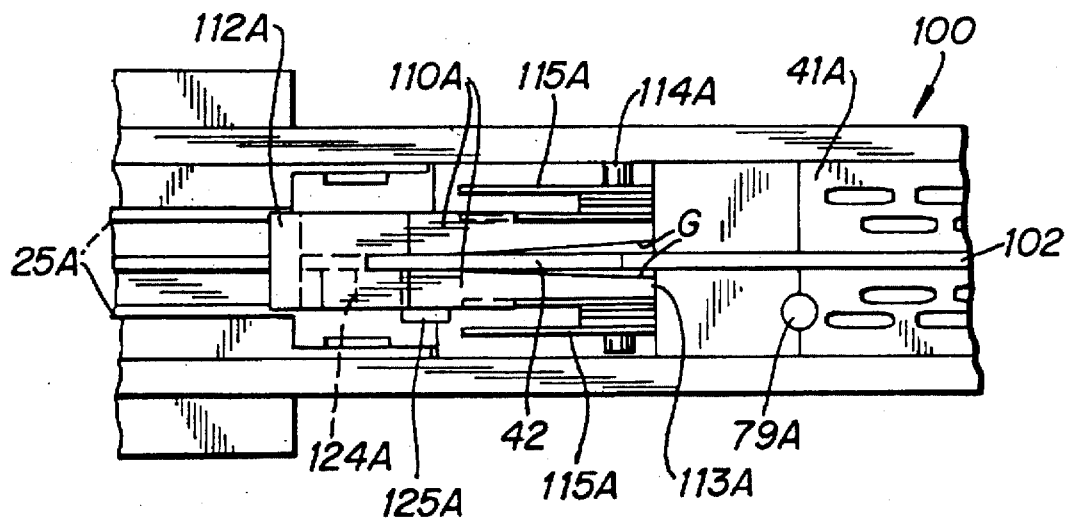
FIG_8
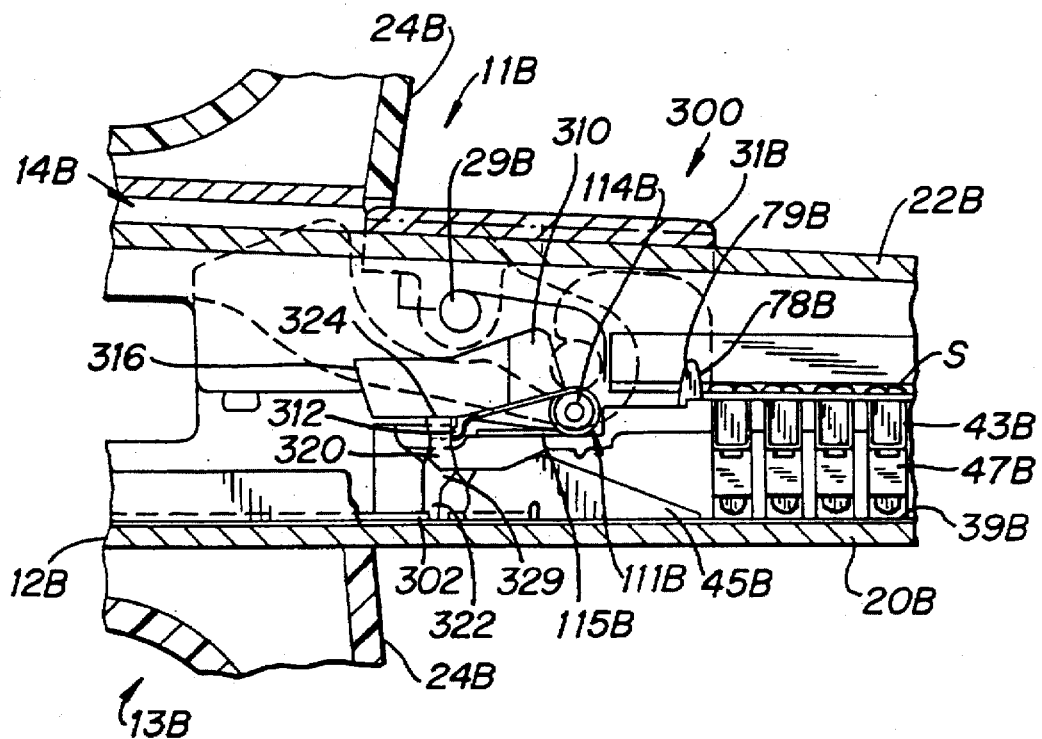
FIG_8A

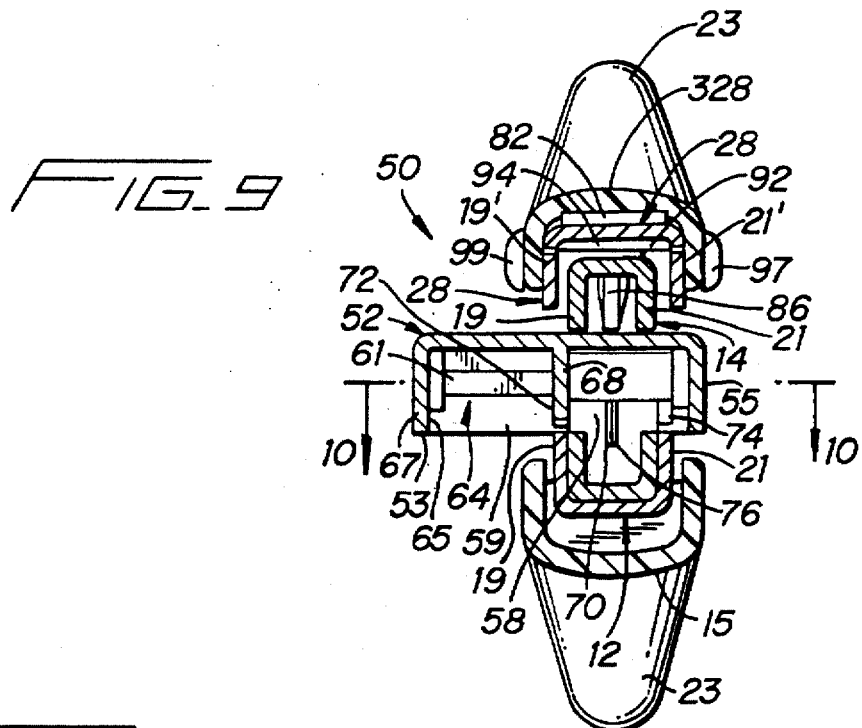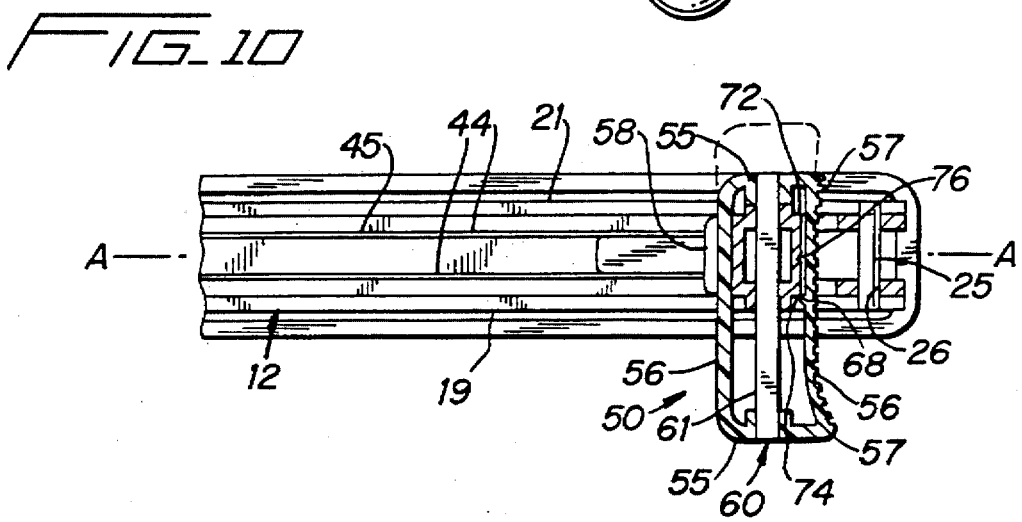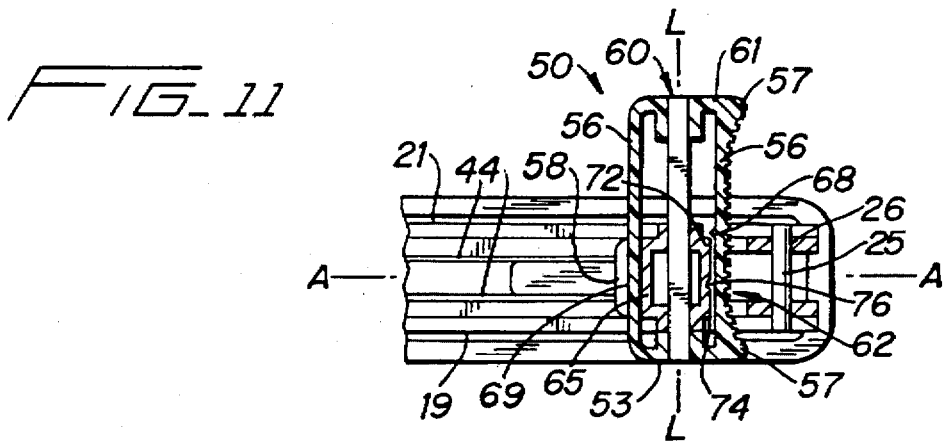

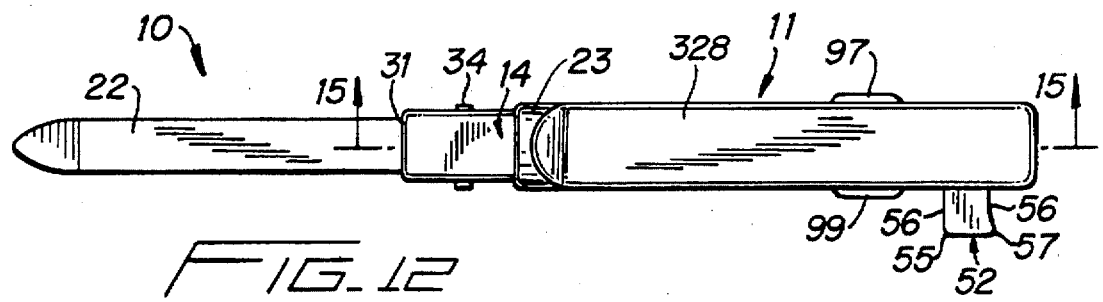
FIG_12
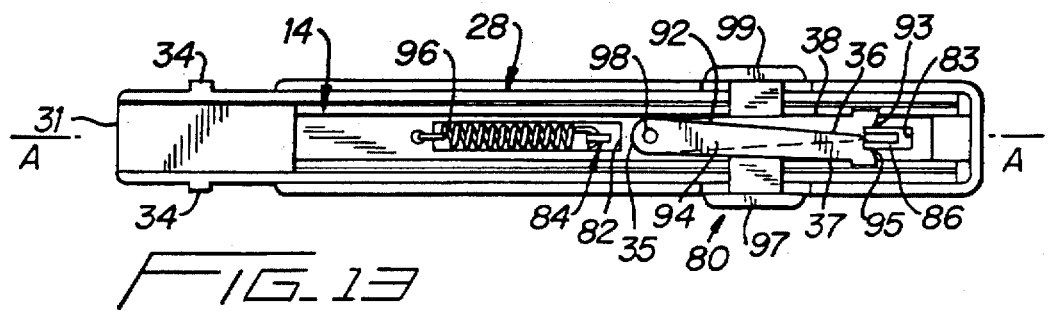
FIG_13
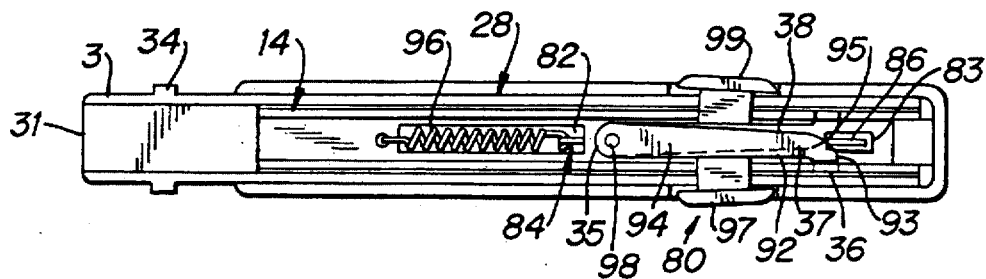
FIG_14
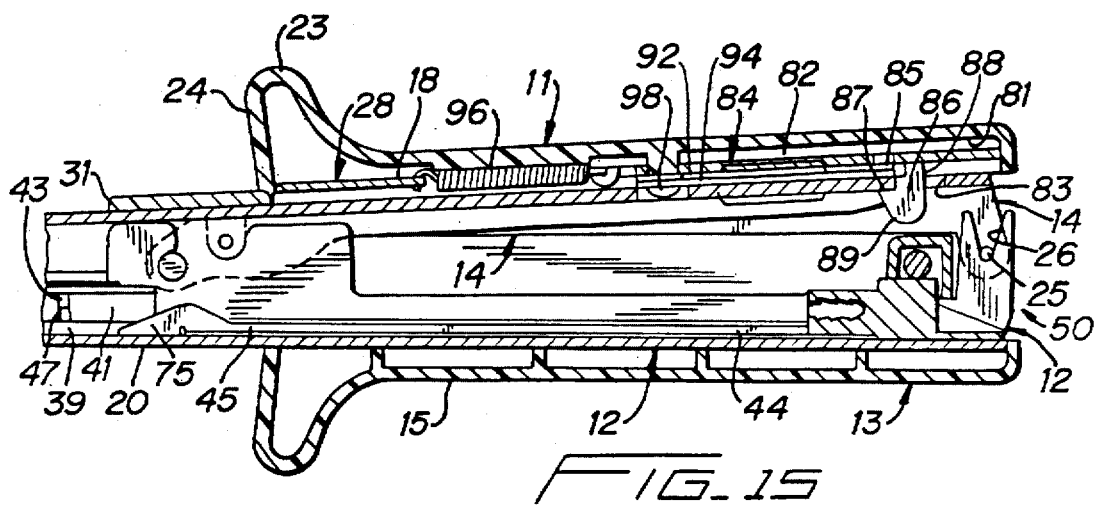
FIG_15

SAFETY DEVICE FOR A SURGICAL STAPLER CARTRIDGE

This a continuation of application Ser. No. 08/270,397 filed Jul. 5, 1994, now U.S. Pat. No. 5,445,304, which is a continuation of application Ser. No. 07/629,597 filed Dec. 18, 1990, now abandoned.

TECHNICAL FIELD

The present invention relates generally to surgical stapling instruments for applying parallel rows of staples through compressed living tissues, and particularly to staple cartridges used to provide the staples for the stapling instruments.

BACKGROUND ART

The art is replete with surgical stapling instruments used for applying parallel rows of staples through compressed living tissue. These types of stapling devices are used, for example, in transecting or reconnecting intestinal, gastric, skin and lung tissue.

One known surgical stapling instrument of this type is well known and is currently available under the trade designation "The ILA Stapler", catalog #3957 by Minnesota Mining and Manufacturing Company, St. Paul, Minn. The use of the stapler is described in the publication entitled "Surgical Stapling, Gastric and Small Bowel Procedures, Volume I", ISBN 0-937433-00-4, Library of Congress Catalog Number 85-082599 available from Minnesota Mining and Manufacturing Company, St. Paul, Minn. the contents of which are expressly incorporated herein by reference. The ILA Stapler and an improvement thereto is described in Redmond et al., U.S. Pat. No. 4,863,088 the entire specification of which is also herein expressly incorporated by reference. That stapling instrument comprises first and second elongate structural members each comprising a handle part and a jaw part projecting from a first end of the handle part. The structural members have pivot means at second ends of their handle parts adapted for free engagement and disengagement in a plane normal to the directions in which the members are elongate, which pivot means afford, when engaged, relative pivotal movement of the structural members in the plane between a closed position with the jaw parts in closely spaced relationship, and an open position spaced farther from each other than in the closed position. An elongate locking member having a pivot point closely adjacent a first end is mounted at its pivot point on the first end of the second structural member for pivotal movement around an axis generally normal to the plane between a locking position generally aligned with the handle part of the second structural member, and a release position with a second end of the locking member spaced from the second end of the second structural member. The first end of the locking member and the handle part of the first structural member adjacent its first end have surfaces adapted, when the pivot means are engaged and the structural members are in their open position, for engagement during movement of the locking member from its release position to its locking position to forcefully move the structural members to their closed position so that high compressive forces can be applied on tissues to be stapled between the jaw parts of the structural members. A means adapted for releasable engagement between the elongate locking member and the second structural member is provided for releasably holding the locking member in its locking position and thus maintain any compressive forces applied between the jaw parts. The stapling instrument is adapted to have a fixed or removable anvil positioned along one of the jaw parts, and a cartridge containing a plurality of staples disposed in rows positioned along the other of the jaw parts in opposition to the anvil, and the cartridge includes manually actuatable means for sequentially ejecting the staples from the cartridge to press the staples against the anvil to engage and close the staples in tissues between the jaw parts when the structural members are in their closed position. Additionally, if desired, the cartridge can include a knife that moves along and bridges between the cartridge and anvil to cut tissues between the rows of applied staples.

Typically the jaw parts of the ILA stapler are positioned adjacent the tissue to be stapled, if necessary the tissue is everted between the stapler jaw parts, the jaw parts are approximated adjacent the tissue to be stapled, and the stapler is clamped on the tissue by moving the jaw parts to the closed position. In some surgical procedures the clamping force results in tissue that is highly compressed to ensure, inter alia, proper hemostasis in the tissues being stapled. The clamping force is present in various degrees in each of the surgical procedures for an ILA type surgical stapler. Such a clamping force causes tissue trauma in the tissue to be stapled, at least to some degree.

The ILA stapler encounters problems because it is difficult to determine when a spent cartridge is loaded in the stapler. Typically a spent cartridge may be inadvertently left in a stapler after it has been fired during a surgical procedure where the stapler is used several times for the same patient. When the stapler is loaded with a spent cartridge and the stapler jaw parts are clamped on both sides of tissue to be stapled, the tissue is subject to the undesirable trauma resulting from the compressive forces created by the jaw parts and the user must disengage the jaw parts, replace the spent cartridge with an unused cartridge and again approximate the stapler adjacent the tissue to be stapled. These additional actions consume precious time during the surgical procedure.

One surgical stapler cartridge lockout device is described in U.S. Pat. No. 4,892,244 which illustrates means for preventing the firing means of a stapler from being fired when the stapler is loaded with a spent stapler cartridge. The use of such a lockout mechanism, however, does not prevent the jaw parts of the stapler from being clamped on the tissue to be stapled when the stapler is loaded with a spent cartridge.

DISCLOSURE OF THE INVENTION

The present invention provides a staple cartridge assembly adapted for use in a surgical stapler having (1) a cartridge retention portion and (2) an anvil portion, the portions being relatively movable between a closed position in which the cartridge and anvil portions are in closely spaced relationship for clamping tissue to be stapled therebetween and an open position with the cartridge and anvil portions spaced farther from each other than in the closed position. The cartridge assembly comprises (1) a firing assembly for firing staples which is movable between a pre-fired and a fired position, (2) a safety member, (3) means mounting the safety member on the cartridge assembly for movement between a free-movement position which affords movement of the cartridge retention portion and the anvil portion between the open and closed position and a blocking position which prevents the cartridge retention portion and the anvil portion from being moved to the closed position, and (4) means for releasably retaining the safety member in the free-movement position and for releasing the safety member to afford movement of the safety member toward the blocking position when the firing assembly is moved from the pre-fired to the fired position such that upon movement of the cartridge retention portion and anvil portion to the open position, the safety member prevents the cartridge portion and the anvil portion from thereafter being moved to the closed position while the stapler is loaded with the spent cartridge. The safety member allows the stapler to be used with or without a knife for cutting between applied rows of staples.

In one embodiment, the staple cartridge assembly includes biasing means for biasing the safety member from the free-movement toward the blocking position, the firing assembly includes a pusher for sequentially pressing the Staples against the anvil portion to engage and close the staples in tissue between the jaw parts when the cartridge retention and anvil portions are in the closed position. In that embodiment of cartridge assembly according to the present invention, the means for releasably retaining the safety member in the free-movement position and for releasing the safety member comprises the pusher having surfaces defining a bearing surface, the safety member having retention surfaces, and a release member having first and second opposite ends, the first end having shoulder surfaces adapted to engage the bearing surface, the second end having latch surfaces adapted to engage the retention surfaces of the safety member. There are also provided means mounting the release member on the cartridge assembly for movement between a holding position in which the latch surfaces are engaged with the retention surfaces to afford retention of the safety member in the free-movement position against the bias of the biasing means and a release position in which the latch surfaces are spaced from the retention surfaces to afford movement of the safety member toward the blocking position. When the firing assembly is moved from the pre-fired to the fired position, the bearing surface engages the first end of the release member and drives the release member from the holding position to the release position.

In another embodiment of the present invention, there is provided an improved staple cartridge assembly adapted for use in a surgical stapler having first and second structural members each being elongate in a first direction, the first structural member having a handle part having first and second ends, the second structural member having a base portion having first and second ends and each of the structural members having a jaw part projecting from their first ends. The jaw parts have proximal ends adjacent the first end of the handle part of the first structural member and the first end of the base portion of the second structural member. Each of the jaw parts have distal ends remote from the proximal ends.

The structural members have pivot means at their second ends adapted for free engagement and disengagement in a plane normal to the first direction for affording, when engaged, relative pivotal movement of the structural members in the plane between a closed position with the jaw parts in closely spaced relationship, and an open position with the jaw parts spaced farther from each other than in the closed position. In the closed position, the handle part of the first structural member and the base portion of the second structural member define a space between the structural members over the majority of the distance between the first and second ends.

An elongate locking member is provided which has first and second ends and a pivot point closely adjacent the first end of the locking member. The pivot point of the locking member is mounted on the second structural member adjacent the first end of the second structural member for pivotal movement around an axis generally normal to the first direction between a locking position generally aligned with the base portion of the second structural member, and a release position with the second end of the locking member spaced from the second end of the second structural member. The first end of the locking member and the handle part of the first structural member adjacent its first end have surfaces adapted, when the pivot means are engaged with the structural members in the open position, for engagement during movement of the locking member from the release position to the locking position to forcefully move the structural members to the closed position. There is also present means adapted for releasable engagement between the elongate locking member and the second structural member for holding the locking member in the locking position.

The first structural member is adapted to receive the staple cartridge assembly and the jaw part of the second structural member is adapted to receive a fixed or removable anvil member having an anvil surface. There is also provided a safety stop surface which may be, for example, adjacent the proximal end of the jaw member of the second structural member or adjacent one end of the anvil.

Like known cartridge assemblies, the staple cartridge assembly according to the present invention comprises a staple housing for enclosing a plurality of staples disposed in rows oriented longitudinally of the jaw part in opposition to the anvil when the structural members are in their closed position. A manually actuatable means including cam like drivers or pushers is adapted to be moved through longitudinal slots in the cartridge body by manually pressing on a shuttle firing assembly fixed at first ends of the pushers. The second ends of the pushers sequentially press the plurality of staples within the staple housing against the anvil to engage and close the plurality of staples in tissues between the jaw parts when the structural members are in the closed position. The pushers are movable in the first direction between a retracted position with the plurality of staples enclosed within the cartridge body and an extended position with the plurality of staples closed within tissue. The shuttle firing assembly is located within the space between the structural members and is adapted to move the pushers from their retracted to their extended positions.

Unlike known cartridge assemblies, the staple cartridge assembly of the present invention comprises a safety member or arm having first and second ends, a base portion adjacent its first end and an abutment surface generally adjacent its second end which is adapted to abut the safety stop surface. The cartridge assembly includes pivotal mounting means for mounting the first end of the safety arm on the cartridge housing for pivotal movement of the safety arm between a pre-fired position for affording movement of the structural members between the closed and open positions and a fired position with the abutment surface of the safety arm adapted to be engaged by the safety stop surface to prevent the structural members from being moved to the closed position. There are also provided biasing means for biasing the safety arm toward the fired position, latch means adapted for releasable engagement between the safety arm and the cartridge housing for retaining the safety arm in the pre-fired position when the pushers are in the retracted position, and release means for releasing the latch means to afford movement of the safety arm from the pre-fired to the fired positions when the pushers are moved from the retracted to the extended position.

BRIEF DESCRIPTION OF THE DRAWING

The present invention will be further described with reference to the accompanying drawing wherein like reference numerals refer to like parts in the several views, and wherein:

FIG. 1 is a perspective view of a first embodiment of surgical stapling instrument for use with the cartridge assembly of the present invention illustrating first and second assemblies of the stapling instrument in a closed position;

FIG. 2 is a side view of the surgical stapling instrument of FIG. 1;

FIG. 3 is a side view of the surgical stapling instrument of FIG. 1 showing the first and second assemblies of the stapling instrument in an open position;

FIG. 4 is an enlarged fragmentary side view of the surgical stapling instrument of FIG. 1 having portions broken away to show details of a first embodiment of cartridge assembly according to the present invention including a safety arm in a pre-fired position;

FIG. 5 is an enlarged fragmentary side view of the surgical stapling instrument of FIG. 1 illustrating the structural members in an open position and having portions broken away to show details of the first embodiment of cartridge assembly with the safety arm in a fired position;

FIG. 8 is an enlarged sectional view of the cartridge assembly of FIG. 7 taken approximately along line 8—8 of FIG. 7 and having portions broken away to show detail;

FIGS. 8A through 8C are fragmentary side views of a third alternative embodiment of the cartridge assembly according to the present invention which sequentially illustrate the operation of the cartridge assembly;

FIG. 9 is an enlarged sectional view of the surgical stapling instrument of FIG. 1 taken approximately along lines 9—9 of FIG. 2;

FIG. 10 is an enlarged partial sectional view of the stapler and cartridge assembly of FIG. 1 taken approximately along line 10—10 of FIG. 9 illustrating the position of the firing body in a first position with solid lines and a middle position with broken lines;

FIG. 11 is an enlarged sectional view of the first embodiment of surgical stapling instrument of FIG. 1 which is similar to FIG. 10 but which illustrate the position of the firing body in a second position;

FIG. 12 is a top view of the surgical stapling instrument of FIG. 1;

FIG. 13 is an enlarged fragmentary sectional view of the surgical stapling instrument of FIG. 1 taken approximately along line 13—13 of FIG. 2 and illustrating a lever lock in a latched position;

FIG. 14 is an enlarged fragmentary sectional view of the surgical stapling instrument and cartridge assembly of FIG. 1 which is similar to FIG. 13 except that FIG. 14 illustrates the lever lock in an unlatched position;

FIG. 15 is an enlarged fragmentary sectional view of surgical stapling instrument for use with the cartridge assembly of FIG. 1 taken along line 15—15 of FIG. 12;

DETAILED DESCRIPTION

Figure 6:
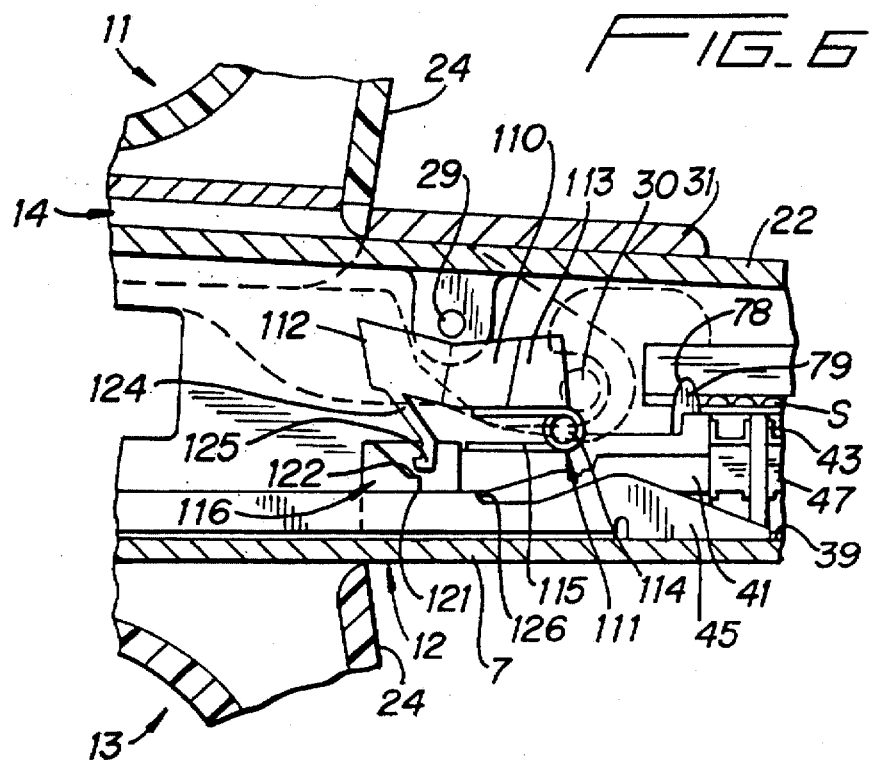
FIG. 6 is an enlarged fragmentary side view of the surgical stapling instrument of FIG. 1 illustrating the structural members in the closed position and having portions broken away to show details of the first embodiment of cartridge assembly with the safety arm in an intermediate position between the pre-fired and the fired positions.

Referring now to FIGS. 1 through 3 of the drawing, there is shown a first embodiment of a surgical stapling instrument 10 for use with a cartridge assembly 2 according to the present invention, generally designated by the reference numerals 2 and 10 and with the surgical stapler 10 comprising two separable assemblies 11 and 13.

According to the present invention there is provided an improved cartridge assembly 2 for use with a surgical stapling instrument 10 comprising first and second elongate structural members 12, 14 having first and second sides 19, 21 with the first structural member 12 comprising a handle part 16 and a jaw part 20 projecting from a first end 7 of the handle part 16, and with the second structural member 14 including a base portion 8 and a jaw part 22 projecting from a first end 3 of the base portion 8. A tissue stop surface 31 is present generally adjacent the first end 3 of the second structural member 14 and is adapted to abut tissue. The tissue stop surface 31 provides means for aligning the tissue to be stapled with respect to the stapler jaw parts 20, 22.

The structural members 12, 14 have pivot means at second ends 5, 9 of the handle part 16 and the base portion 8 comprising two opposite axially parallel outwardly projecting pins 25 on the second structural member 14 and generally U-shaped journal surfaces 26 on the first structural member 12 adapted and positioned for free engagement and disengagement in a plane normal to the directions in which the structural members 12 and 14 are elongate, which pivot means affords, when engaged, relative pivotal movement of the structural members 12, 14 in the plane normal to the directions in which the structural members 12 and 14 are elongate between a closed position (FIGS. 1 and 2) with the jaw parts 20, 22 in closely spaced relationship, and an open position (FIG. 3) with the jaw parts 20, 22 spaced farther from each other than in the closed position.

An elongate locking member 28 having a pivot point at a pin 29 closely adjacent a first end 4 of the locking member 28 is mounted by the pin 29 on the first end 3 of the second structural member 14 for pivotal movement around an axis generally normal to the plane between a locking position (FIGS. 1 and 2) generally aligned with the base portion 8 of the second structural member 14, and a release position (FIG. 3) with the second end 6 of the locking member 28 spaced from the second end 5 of the second structural member 14. The elongate locking member 28 includes a handle part 18 and a lever or handle cover 328 is attached to the handle part 18. A lever stop 34 is attached to the second structural member 14 to prevent the locking member from pivoting forward from the open position and pinching tissue.

The first end 4 of the locking member 28 and the first end 7 of the first structural member 12 have surfaces provided by two opposite axially parallel inwardly projecting pins 30 on the handle part 18 and side surfaces of generally U-shaped journal surfaces 32 on the first structural member 12 opening toward the second end 9 of the first structural member 12, adapted, when the pivot means are engaged with the structural members 12, 14 in the open position, for engagement during movement of the locking member 28 from its release position (FIG. 3) to its locking position (FIG. 2) to forcefully move the structural members 12, 14 to their closed position so that high compressive forces can be applied to tissues between the jaw parts 20, 22 of the structural members 12, 14.

A handle cover 15 is attached to the handle part 16 of the first structural member 12. The handle cover 328 is attached to the handle part 18 of the locking member 28 and is similar in shape to the handle cover 15. The handle covers 15, 328 have manually engageable projections 23 having engagement surfaces 24 disposed generally at an included angle of less than ninety degrees with respect to the direction of elongation of the jaw parts 20, 22, preferably eighty-five degrees. The engagement surfaces 24 of the handle covers 15, 328 are adapted to be engaged with the fingers of a user's hand while the thumb of that hand is used to operate an adjustable firing body assembly 50 which is used to fire staples 43. The angle between the jaw parts 20, 22 and the engagement surfaces 24 is less than ninety degrees to provide grasping means for the user's fingers to provide an incline to prevent the user's fingers from slipping or sliding from the handle covers 15, 328. The handle covers 15, 328 may be constructed from any suitable material such as, but not limited to, polycarbonate or ABS plastic.

The stapling instrument 10 comprises means for releasable engagement between the elongate locking member 28 and the second structural member 14, generally designated by the reference number 80. As shown in FIGS. 12–15, that means comprises a dual-sided lever lock release assembly 80 comprising surfaces defining a slot 83 in the second structural member 14 adjacent the second end 5 of the second structural member 14, and a lever lock 84 having a generally rectangular planar base portion 82 having a longitudinal axis. The base portion 82 is located within a chamber 81 between the handle part 18 and the lever cover 328, and, a hook portion 86 is connected to the base portion 82 by being integral therewith. The hook portion 86 is positioned generally normal to the base portion 82 and has a retaining surface 87 adapted to engage a surface at one end of the slot 83 of the second structural member 14 to retain the elongate locking member 28 in the locking position (FIG. 15). The lever lock 84 is adapted to move axially between an unlatched position (FIG. 14) to afford movement of the elongate locking member 28 to the release position (FIG. 3) and a latched position (FIGS. 13 and 15) to retain the elongate locking member 28 in the locking position (FIG. 2). The handle part 18 of the elongate locking member 28 has surfaces defining an aperture 88 communicating with the chamber 81 and located adjacent the second end 6 of the elongate locking member 28 which affords passage of the hook portion 86.

The dual-sided lever lock release 80 is located on first and second sides 19', 21' of the elongate locking member 28 and comprises first 92 and second 94 release arms each having first and second opposite ends 35, 36, and first and second opposite side surfaces 37, 38. The second ends 36 of the release arms 92, 94 include camming surfaces 93, 95, and the first ends 35 of the release arms 92, 94 are pivotally attached to the handle part 18 of the elongate locking member 28 by a pin 98 to afford movement between an engaged position (FIG. 14) with camming surface 93 or 95 in engagement with the lever lock 84 to unlatch the lever lock 84 and a disengaged position (FIG. 13) with the camming surfaces 93 or 95 disengaged or spaced from the lever lock 84. Preferably the release arms 92, 94 are constructed to remain slightly engaged with the lever lock 84 when they are in the disengaged position to prevent the camming surfaces 93 or 95 from sliding out of contact with the lever lock 84.

The lever lock 84 includes a shoulder surface 85 adjacent the hook portion 86 for receiving the camming surfaces 93, 95 when either of the release arms 92 or 94 are moved to the engaged position. The release arms 92, 94 move independently of each other and thus, although FIG. 14 'shows both release arms 92, 94 moved to the engaged position, the user need only actuate one of the release arms 92 or 94 to release or unlatch the lever lock 84 from the second structural member 14. This feature affords independent release of the elongate locking member 28 from either of its sides 19', 21' and provides alternative, opposite release means when using the stapler 10 in a crowded, cramped location.

First and second release buttons 97, 99 are mounted on the release arms 92, 94 adjacent the sides 19', 21' of the elongate locking member 28 for movement between first and second positions with respect to the locking member 28. The first button 97 is mounted to the second release arm 92 along its first side 38 and the second button 99 is connected to the first release arm 94 along its second side 37 so that movement of either of the buttons 97, 99 from the first to the second position relative to the locking member 28 will pivotally move the associated release arm 92 or 94 from the disengaged to the engaged position and thus drive the lever lock 84 from the latched position to the unlatched position.

The dual-sided lever lock release assembly 80 includes biasing means for biasing the lever lock 84 axially toward the latched position in the form of a coil spring 96 connected to the elongate locking member 28 and to one end of the lever lock 84. The coil spring 96 is placed in tension to bias the lever lock 84 toward the latched position. The biasing means may comprise any suitable means including but not limited to a leaf spring, a coil spring, an extension spring, a compression spring or a torsion spring.

The hook portion 86 comprises camming surface 89 adapted to engage the surfaces defining the slot 83 of the second structural member 14 when the elongate locking member 28 is moved from the release to the locking positions. The camming surface 89 moves the lever lock 84 from the latched position to the unlatched position against the bias of the coil spring 96 to afford passage of the hook portion 86 from one side of the slot 83 in the second structural member 14 to the other to thereby afford engagement between the retaining surface 87 of the hook portion 86 and the surfaces of the second structural member 14 surrounding the slot 83 when the elongate locking member 28 is moved from the release position (FIG. 3) to the locking position (FIG. 2). The coil spring 96 biases the lever lock 84 axially toward the latched position and thus causes a tactile "click" when the lever lock 84 slides to the latched position and the retaining surface 87 engages the surfaces surrounding the slot 83.

The second structural member 14 is adapted to have an elongate fixed or removable anvil 40 positioned over and along the jaw part 22 to form the first assembly 11, and the jaw part 20 of the first structural member 12 has an elongate groove 39 adapted to receive a cartridge housing or body 41 of the improved cartridge assembly 2 according to the present invention to form the second assembly 13. There is also provided a safety stop surface 33 (FIG. 5), later to be explained in greater detail located adjacent the proximal end of the jaw member 20 of the second structural member 12 or adjacent one end of the anvil 40. Alternatively, the cartridge body 41 may be integral with the first structural member 12.

The cartridge body 41 contains a plurality of staples 43 disposed in rows oriented longitudinally of the jaw part 20 in opposition to the anvil 40 when the structural members 12, 14 are in their closed position. Also, the cartridge assembly 2 includes manually actuatable means including cam-like drivers or pushers 45 having first 44 and second 75 longitudinally spaced end portions. The pushers 45 are adapted to move longitudinally along the first jaw part 20 with the second end portion 75 sequentially pressing the staples 43 against the anvil 40 to engage and close the staples 43 in tissue between the jaw parts 20, 22 with the first end portion 44 moving between the handle part 16 and the base portion 8. The pushers 45 are adapted to be moved longitudinally through slots in the cartridge body 41 by manually pressing on the adjustable firing handle assembly 50.

The adjustable firing handle assembly 50 is connected to the first end portion 44 of the pushers 45. When the shuttle firing handle assembly 50 is manually pressed to move the firing handle body 52 from the pre-fired position (FIG. 2) to the fired position, the drivers or pushers 45 sequentially eject the staples from the cartridge body 41 by means of camming plungers 47 under the staples 43. The camming plungers 47 push the staples 43 toward a surface of the cartridge body 41 opposite the anvil 40 and thereby press the ejected staples 43 against specially shaped surfaces S on the anvil 40 to engage and close the staples 43 in tissues between the jaw parts 20, 22 when the structural members 12, 14 are in their closed position.

The firing handle assembly 50 comprises the elongate firing handle body 52 within a space between the handle part 16 of the first structural member 12 and the base portion 8 of the second structural member 14 for moving the pushers 45 from the retracted (FIG. 2) to the extended positions. The firing handle body 52 has a longitudinal axis L (FIG. 11) transverse to the direction-in which the structural members 12, 14 are elongate. The firing handle body 52 has generally planar and opposite first 53 and second 55 end portions situated perpendicular to the longitudinal axis L of the firing handle body 52. A firing handle adapter 58 is attached to first end portion 44 of the pushers 45 and is adapted to connect the firing handle body 52 to the pushers 45.

A means 60 is provided which mounts the firing handle body 52 to the firing handle adapter 58 for releasable, reciprocating lateral movement of the firing handle body 52 along the longitudinal axis L in the form of a rod 61 extending between end portions 53 and 55 and located within an opening 69 in the firing handle adapter 58. A detent means 62 is also provided which releasably secures the firing handle body 52 in a first position (FIG. 11) with the first end portion 53 of the firing handle body 52 generally adjacent a first side 19 of the structural members 12, 14 and a second position (FIG. 10, solid lines) with the second end portion 55 of the elongate firing handle body 52 generally adjacent a second side 21 of the structural members 12, 14.

The structural members 12, 14 have an axis A (FIGS. 10 and 12) extending generally in the first direction along a middle portion of the stapler 10. The detent means 62 also releasably secures the firing handle body 52 in a middle position (FIG. 10, dashed lines) midway between the first and second positions at which parts of the first and second portions 53 and 55 of the firing body 52 project beyond both the first and second sides 19, 21. When the elongate firing handle body 52 is placed in the middle position, the end portions 53 and 55 are located laterally beyond the sides 19', 21' of the locking member 28 and provide surfaces on both sides of the stapler 10 for manually pressing on the elongate firing handle body 52.

Rectangular side walls 56 are present on the elongate firing handle body 52 which cooperate with the first and second end portions 53, 55 to form a rectangular box-shape 64 open along the side walls 56 into a cavity 59. The elongate firing handle body 52 has inside 65 and outside 67 surfaces, and the detent means 62 includes detent surface 68 which extends beyond the inside surface 65 of one of the rectangular side walls 56. It should be noted that the firing body 52 may comprise any suitable shape including but not limited to square, triangular, arcuate and combinations of those shapes.

The firing handle adapter 58 has a neck portion 70 having first 72 and second 74 opposite generally planar flank walls, and surfaces which define a notch 76 adapted to receive the detent surface 68 of the firing handle body 52. As shown in FIG. 9, the neck portion 70 is adapted to extend into the cavity 59 of the firing handle body 52.

The first and second opposite planar flank walls 72, 74 are releasably secured between the detent surface 68 and the inner surface 65 of the second end portion 55 of the firing handle body 52 when the firing handle body 52 is in the first position, and the first and second opposite planar flank walls 72, 74 are releasably secured between the detent surface 68 and the inner surface 65 of the first end portion 53 of the firing handle body 52 when it is in the second position.

The means 60 mounting the firing handle body 52 to the firing handle adapter 58 for manual movement of the elongate firing handle body 52 along its longitudinal axis L comprises the cylindrical pin or rod 61 attached at its ends to the end portions 53, 55 of the firing handle body 52, and the neck portion 70 of the adapter 58 having surfaces defining an opening 69 adapted to receive the cylindrical pin 61.

In the middle position, the detent means 62 mounts the elongate firing handle body 52 to the firing handle adapter 58 with detent surface 68 engaged with the notch 76 of the neck portion 70 and with the first 53 and second 55 end portions of the elongate firing handle body 52 generally equidistant from the axis A of the stapler 10. As shown in FIG. 10, in the middle position parts of both the first and second end portions 53, 55 project beyond both the first and second sides 19, 21.

The side wall 56 of the firing handle body 52 proximate the user includes flared edges 57 near the end portions 53, 55. The flared edges 57 provide means for grasping the firing handle body 52 with, for example, the user's thumbs and are flared outward to deter the user's thumbs from sliding laterally from the firing handle body 52. The flared edges 57 also deter the detent surface 68 from disengaging the notch 76 when the firing body 52 is in the first or the second position as manual pressure on the flared edges 57 directs the force on firing handle body 52 in a direction which tends to retain the firing body 50 in its original position.

During use of the stapler 10, the engagement surfaces 24 of the handle covers 15, 328 are engaged by the fingers of a user's hand while the user's thumb is used to operate the firing handle body 52. The user may use only one hand to operate the firing handle body 52 when the firing handle body 52 is in the-first or second positions. Such a feature is desirable for users who prefer to use only either their right or left hand when firing the stapler 10. When the firing handle body 52 is in the middle position, however, both of the user's thumbs may be used to operate the firing handle body 52 from both sides 19, 21 of the structural members 12, 14 to afford symmetrical manual pressing on the firing body 52 about the axis A of the first and second structural members 12, 14. Affording a user the capacity to symmetrically press on the firing handle body 52 from both sides of the axis A of the first and second structural members 12, 14 assists the user in controlling the position and stability of the stapler 10 and provides more effective firing of the stapler 10 when it is used, for example, in procedures which require a relatively large force to move the firing handle body 52 from the pre-fired to the fired position.

A first embodiment of the novel structure of the cartridge assembly 2 which allows the cartridge assembly 2 to prevent accidental tissue trauma after the structural members 12, 14 have been moved to the open position is shown in FIGS. 4 through 6. The first embodiment of cartridge assembly 2 comprises a safety member or arm 110 having first and second ends and a base portion 113 adjacent its first end. The safety arm 110 includes an abutment surface 112 adjacent its second end adapted to abut the safety stop surface 33 which is adjacent the proximal end of the jaw 22.

Pivotal mounting means 114 mount the first end of the safety arm 110 on the cartridge housing 41 for pivotal movement of the safety arm 110 between a "free-movement" or pre-fired position (FIG. 4) for affording movement of the structural members 12 and 14 between the closed and open positions and a "blocking" or fired position (FIG. 5) with the abutment surface 112 of the safety arm 110 adapted to engage the safety stop surface 33. FIGS. 4 through 6 show biasing means 111 for biasing the safety arm 110 toward the fired position in the form of two torsion springs 115 each attached at opposite ends to the cartridge housing 41 and to the safety arm 110. The sides of the safety arm 110 may include laterally extending shoulder surfaces to connect one end of the torsion spring 115 to the safety arm 110. The other end of the springs 115 may be attached to the cartridge housing 41. The biasing means 111 may be any suitable means including, but not limited to a coil spring, a leaf spring or a torsion spring. Moreover, the biasing means 111 need not comprise two torsion springs but may instead comprise a single spring.

A latch means 116 is provided for releasable engagement between the safety arm 110 and the cartridge housing 41 for retaining the safety arm 110 in the pre-fired position while the pushers 45 remain in the retracted position. Release means 120 is provided for releasing the latch means 116 to afford movement of the safety arm from the pre-fired toward the fired position when the pushers 45 are moved from the retracted to the extended position. The latch means 116 comprises retention surfaces 121 on the cartridge housing 41 at a distal end of a ledge 122, and an integral flexible projecting portion 124 located on the safety arm 110 and having a distal end portion 125. The projecting portion 124 affords generally pivotal movement of the end portion 125 between a latched position (FIG. 4) with the end portion 125 engaging the retention surfaces 121 to retain the safety arm 110 in the pre-fired position, and an unlatched position (FIGS. 5 and 6) with the end portion 125 spaced from the retention surfaces 121 to afford movement of the release arm 110 toward the fired position under the influence of the biasing means 111.

The safety arm 110 and the projecting portion 124 may be constructed from any suitable material, such as, but not limited to polycarbonate or polyetherimide. The material should have characteristics which provide the projecting portion 124 with a leaf spring like bias toward the latched position (FIG. 4) to retain the end portion 125 in engagement with the retention surfaces 121 until the release means 120 moves the end portion 125 to the unlatched position. The material should be flexible to provide flexing of the projecting portion 124 near the interface or juncture between the safety arm 110 and the projecting portion 124 without cracking or breaking.

The release means 120 may comprise cam surfaces 126 located on one of the pushers 45 adapted to engage the end portion 125 of the flexible projecting portion 124 to move the end portion 125 from the latched to the unlatched position during movement of the pushers 45 from the retracted to the extended positions.

FIG. 6 illustrates the safety arm 110 in an intermediate position between the pre-fired and fired positions. During movement of the pushers 45 from the retracted to the extended positions, the latch means 116 releases the safety arm 110 and the biasing means 111 moves the safety arm 110 from the pre-fired position toward the fired position. While the first and second structural members 12, 14 remain in the closed position, such as shown in FIG. 6, the safety arm 110 is not permitted to move completely to the fired position because it engages surfaces on the first assembly 11. Instead, the safety arm 110 is held in the intermediate position as shown in FIG. 6. Once the first and second structural members 12, 14 are moved from the closed (FIGS. 1 and 2) to the open (FIG. 3) position, the safety arm 110 will move under the influence of the biasing means 111 to the fired position. Thereafter, any attempt to place the first and second structural members 12, 14 in the closed position while the first structural member 12 remains loaded with the spent cartridge will be thwarted since the abutment surface 112 will be in a position to contact the safety stop surface 33 on the second structural member 14. Thus, the safety arm 110 prevents the first and second members 12, 14 from moving to the closed position (FIG. 5). This feature of the present invention prevents accidental tissue trauma as the first and second members 12, 14 cannot be clamped on tissue while the stapler 10 is loaded with a spent cartridge.

Once the safety arm 110 is moved to the intermediate position, the leaf spring like bias of the projecting portion 124 will cause the projecting portion 124 to move to a relaxed or unlatched position. In the relaxed or unlatched position, the end portion 125 will engage the ledge 122 to prevent the safety arm 110 from being placed in the pre-fired position should a user attempt to reset the safety arm 110 in the pre-fired position after the cartridge assembly 2 has been fired. The cartridge assembly 2 may also include means for preventing the safety arm 110 from resetting in the pre-fired position once the stapler has been fired in the form of having cam surfaces (not shown) adjacent the end portion 125 of the projecting portion 124 and on the ledge 122 which tend to cause the end portion 125 to move away from the retention surfaces 121 at the distal end of the ledge 122 should a user attempt to reset the safety member 110 in the pre-fired position. This feature of the present invention also discourages a user from defeating the safety mechanism of the present invention to thereby provide a safer device.

In order to align the specially shaped surfaces S on the anvil 40 with their corresponding opposite staples 43 in the cartridge housing 41, the cartridge assembly 2 is provided with an alignment pin 79 located adjacent a proximal end of the jaw part 20. The pin 79 is adapted to be received in an aperture 78 in the anvil 40 and the jaw part 22.

FIG. 6 illustrates the safety arm 110 engaging the pin 29 which mounts the elongate locking member 28 to the second structural member 14. The pin 29 includes surface portions which are engaged by the safety arm 110 at the intermediate release position during the movement of the safety arm 110 from the pre-fired to the fired positions. Once the structural members are moved to the open position, the safety arm 110 will completely move to the fired position (FIG. 5). The safety arm 110 need not engage the pin 29 when it is in the intermediate position and may engage any suitable surface on the stapler 10.

Figure 7:
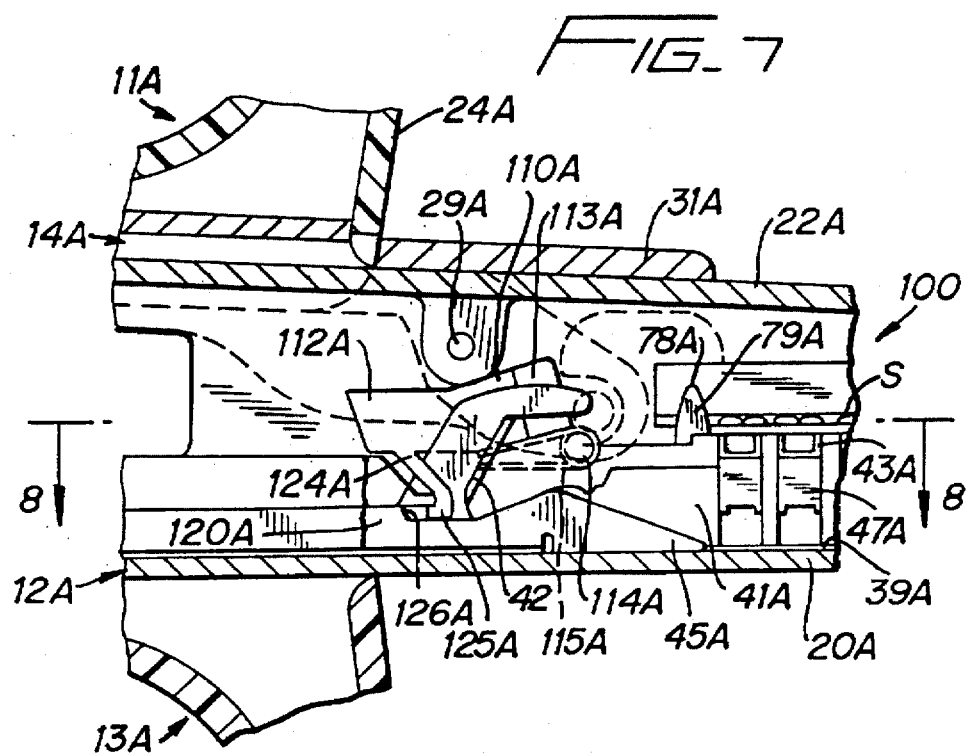
FIG. 7 is an enlarged fragmentary side view of a second alternative embodiment of the cartridge assembly according to the present invention having portions broken away to show detail and illustrating a knife.

Referring now to a second embodiment of cartridge assembly shown in FIGS. 7 and 8, generally designated by the reference number 100, the cartridge assembly 100 may optionally include a knife 42 (FIGS. 7 and 8) that is fixed to one end of a drive rod. The drive rod is fixed at one end to the firing handle assembly (not shown but similar to reference character 50 shown in FIGS. 9 through 11) and fixed at the other end to the knife 42 so that manual movement of the firing handle body (not shown but similar to reference character 52 shown inn FIGS. 9 to 11) causes the pushers or drivers 45A to eject and close the staples 43A and also causes the knife 42 to move along the jaw parts 20A, 22A with the distal end of the knife 42 in a slot or channel 102 in the anvil 40 to cut tissues between the rows of applied staples 43A. As shown in FIG. 8, the alignment pin 79A is offset from the middle portion of the cartridge housing 41A to afford passage of the knife 42 in the slot 102.

FIG. 8 illustrates that the projecting portion 124A/125A is located on a side of the safety arm 110A and is offset from a middle portion of the cartridge assembly 2 to afford clearance for an optional knife or blade which may be included in the second embodiment of the cartridge assembly of the present invention. The pushers 45A are laterally spaced which provides clearance for a drive rod for the optional knife. The pushers may comprise a unitary, monolithic structure connected by a bottom plate or may comprise independent separable L-shaped assemblies.

The cartridge assembly 100 of FIG. 8 has many parts that are essentially the same as the parts of the cartridge assembly 2 and which have been identified by the same reference numeral to which the suffix "A" has been added. The cartridge assembly 100 comprises surfaces defining a longitudinal channel or slot 102 extending in the direction of elongation of jaw parts 20A, 22A though a middle portion of the cartridge body 41A, and a blade or knife 42 having a leading and trailing edge which is situated within the channel 102. The channel 102 may be present in both the first 2 and second 100 embodiments of cartridge assemblies according to the present invention to afford convenient construction and assembly of the cartridge assemblies.

The blade 42 has a cutting surface on its leading edge for cutting tissue between applied rows of staples 43A, and the blade 42 is adapted to travel within the channel 102 between a retracted position adjacent the proximal end of the jaw part 20A of the first structural member 12A and an extended position adjacent the distal end of the jaw part 20A of the first structural member 12A.

The latch means 116A and the release means 120A are also offset from the slot or channel 102 to afford clearance for the blade or knife 42 and its associated drive rod. The safety member 110A also has a groove G to accommodate the blade 42. When the optional knife 42 is included, it is especially important to prevent the stapler 10 from being fired while loaded with a spent cartridge. Firing a stapler 10 while it is loaded with a spent stapler cartridge that includes a knife may lead to serious adverse consequences such as unnecessarily damaged tissue, hemorrhage and loss of time.

Alternatively, when the cartridge assembly includes the optional blade or knife 42, the means for releasably retaining the safety member in the free-movement position and for releasing the safety member may comprise surfaces defining a retention groove (not shown) on the trailing edge of the blade which are adapted to engage shoulder surfaces on the safety member. When the blade is moved from its retracted toward its extended position, the retention groove releases the shoulder surfaces and afford movement of the safety member toward its fired position.

Figure 8B:
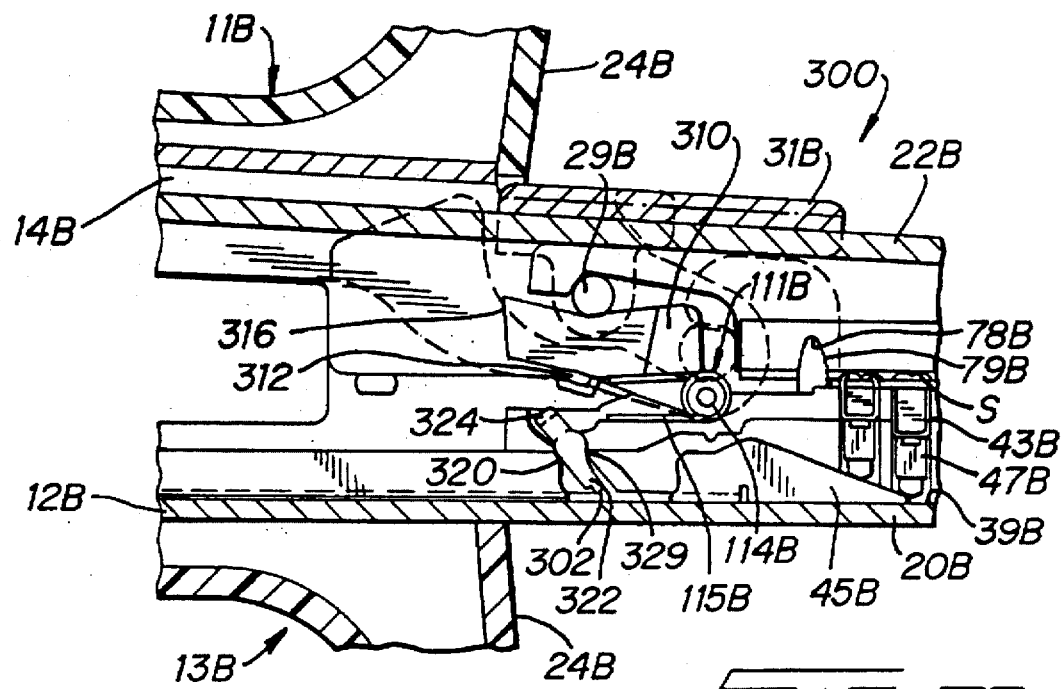
Figure 8C:
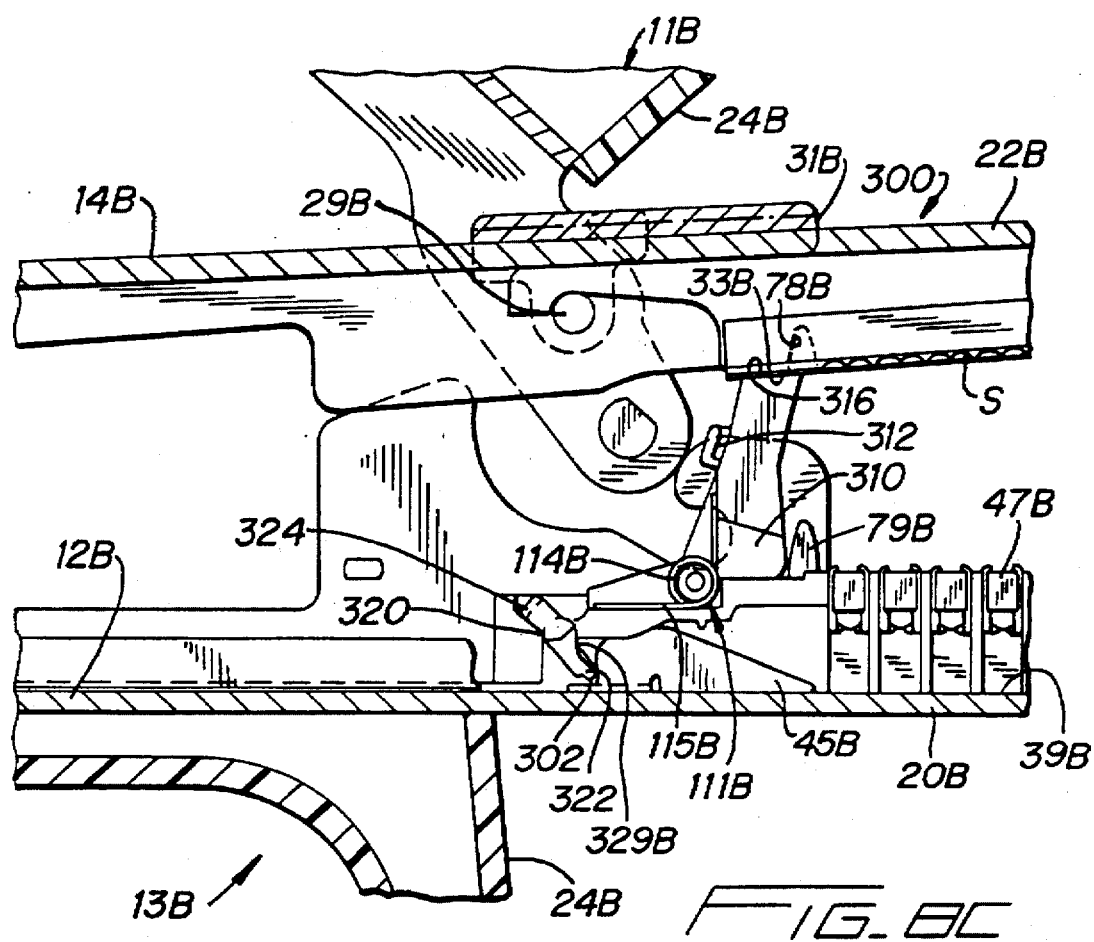

FIGS. 8A through 8C illustrate a third embodiment of cartridge assembly according to the present invention generally designated by the reference number 300 which has many parts that are essentially the same as the parts of the cartridge assembly 2 and which have been identified by the same reference numeral to which the suffix "B" has been added.

The cartridge assembly 300 comprises biasing means 111B which may include, for example, a torsion spring 115B, for biasing the safety member 310 from the free-movement (FIG. 8A) toward the blocking (FIG. 8C) position. The firing assembly includes a plurality of pushers 45B for sequentially pressing the staples 43B against the anvil portion 22B to engage and close the staples 43B in tissue between the jaw parts 20B, 22B when the cartridge retention 12B and anvil 14B portions are in the closed position (FIG. 8A). A means for releasably retaining the safety member 310 in the free-movement position and for releasing the safety member 310 is present and comprise the pushers 45B having surfaces defining a bearing surface 302 located for example, on a bottom plate which connects the pushers 45B by being integral therewith, the safety member 310 having retention surfaces 312, and a release member 320 having a first 322 and second 324 opposite ends. The first end 322 of the release member 320 has shoulder surfaces adapted to engage the bearing surface 302, and the second end 324 has latch surfaces adapted to engage the retention surfaces 312 of the safety member 310.

Means 329 mount the release member 320 on the cartridge assembly 300 for movement between a holding position (FIG. 8A) in which the latch surfaces are engaged with the retention surfaces 312 to afford retention of the safety member 310 in the free-movement position against the bias of the biasing means 111B and a release position (FIGS. 8B and 8C) in which the latch surfaces are spaced from the retention surfaces 312 to afford movement of the safety member 310 toward the blocking position (FIG. 8C).

FIGS. 8A and 8B sequentially illustrate the firing assembly being moved from the pre-fired toward the fired position during which the bearing surface 302 engages the first end 322 of the release member 320 and drives the release member 320 from the holding position (FIG. 8A) to the release (FIGS. 8B and 8C) position. FIG. 8B illustrates the safety member 310 in an intermediate, middle position between the free-movement and blocking positions. The safety member 310 will move under the bias of the biasing means 111B to the intermediate position after the firing assembly has moved from the pre-fired to the fired position but before the cartridge retention 12B and anvil 14B portions of the stapler 10 are moved from the closed (FIGS. 8A and 8B) to the open position (FIG. 8C).

FIG. 8C illustrates the blocking position of the safety member 310 after the firing assembly has moved from the pre-fired toward the fired position and after the cartridge retention 12B and anvil 14B portions of the stapler 10 have been moved from the closed to the open position. In the blocking position, the abutment surface 316 of the safety member 310 engages the safety stop surface 33B on the first assembly 11B. The cartridge assembly 300 thus prevents the jaw portions 20B and 22B from traumatizing tissue while the stapler 10 is loaded with a spent cartridge.

Figure 16:
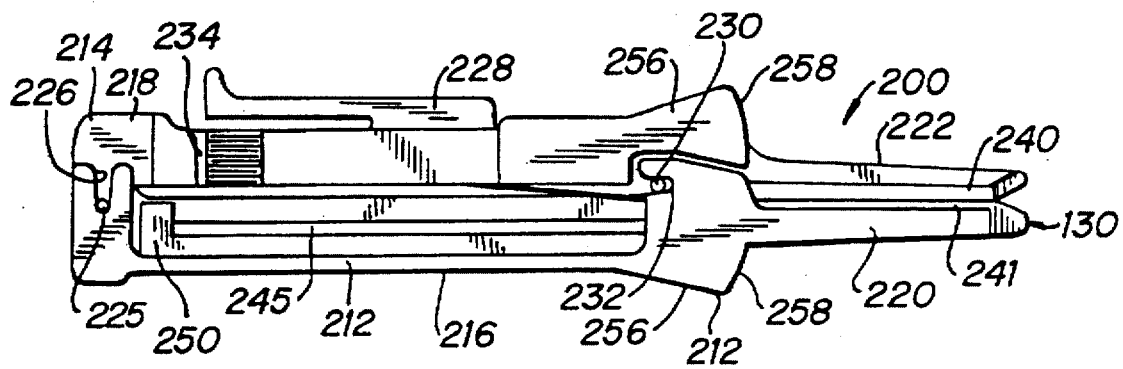
FIG. 16 is a side view of a second embodiment of surgical stapling instrument for use with the cartridge assembly according to the present invention showing two assemblies of the instrument in a closed position.
Figure 17:
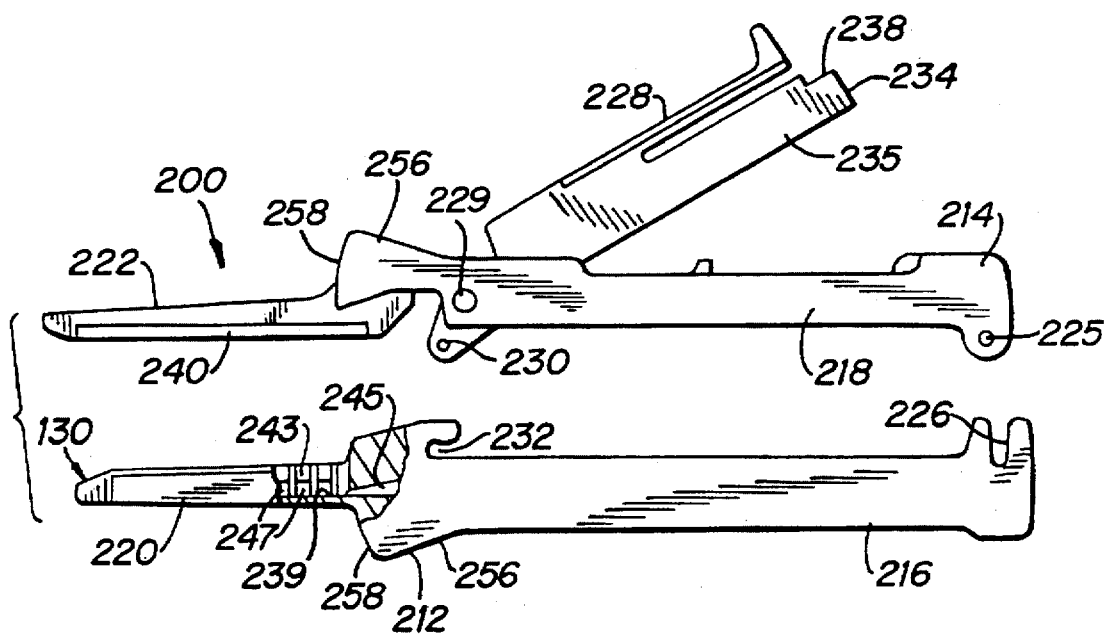
FIG. 17 is a second opposite side view of the surgical stapling instrument of FIG. 16 showing the two assemblies of the instrument separated from each other and having parts broken away to show detail.

The cartridge assembly of the present invention may also be described in combination with the known "ILA Stapler". The structure of the stapling instrument 200 shown in FIGS. 16 and 17 and as described below in this Detailed Description portion of this specification is essentially the same as that of the surgical stapling instrument sold under the trade designation "The ILA Stapler" by Minnesota Mining and Manufacturing Company, St. Paul, Minn. That stapler comprises first and second elongate structural members 212, 214 each comprising a handle part 216 and 218 and a jaw part 220 and 222 respectively projecting from a first end of the handle part 216 or 218. The structural members 212 and 214 have pivot means at second ends of their handle parts 216 and 218 comprising two opposite axially parallel outwardly projecting pins 225 on the second structural member 214 and generally U-shaped journal surfaces 226 on the first structural member 212 adapted and positioned for free engagement and disengagement in a plane normal to the directions in which the structural members 212 and 214 are elongate, which pivot means affords, when engaged, relative pivotal movement of the structural members 212, 214 in the plane normal to the directions in which the structural members 212 and 214 are elongate between a closed position (FIG. 16) with the jaw parts 220,222 in closely spaced relationship, and an open position with the jaw parts 220, 222 spaced farther from each other than in the closed position. An elongate locking member 228 having a pivot point at a pin 229 closely adjacent a first end of the locking member 228 is mounted by the pin 229 on the first end of the second structural member 214 for pivotal movement around an axis generally normal to the plane between a locking position (FIG. 16) generally aligned with the handle part 218 of the second structural member 214, and a release position (not shown) with the second end of the locking member 228 spaced from the second end of the second structural member 214.

The first end of the locking member 228 and the handle part 216 of the first structural member 212 adjacent its first end have surfaces provided by two opposite axially parallel outwardly projecting pins 230 on the locking member 228 and side surfaces of generally U-shaped journal surfaces 232 on the first structural member 212 opening toward the second end of the first structural member 212, adapted, when the pivot means are engaged with the structural members 212, 214 in the open position, for engagement during movement of the locking member 228 from its release position to its locking position to forcefully move the structural members 212, 214 to their closed position so that high compressive forces can be applied to tissues between the jaw parts 220, 222 of the structural members 212, 214.

A means adapted for releasable engagement between the elongate locking member 228 and the second structural member 214 is provided (FIGS. 16 and 17) in the form of an edge abutment surface 238 at one end of a cam 234 on a cantilevered flexible part 235 of the locking member 228. The surface 238 engages an edge abutment surface (not shown) at one end of a cam (not shown) on the second structural member 214 to releasably hold the locking member 228 in its locking position and to maintain the compressive forces applied between the jaw parts 220, 222.

Like the stapler 10 the "ILA" stapler 200 includes manually engageable projections 256 having engagement surfaces 258 disposed generally at right angles to the direction of elongation of the first and second structural members 212, 214 and facing the jaw parts 220, 222. The engagement surfaces 258 of the first structural member 212 and the second structural member 214 are adapted to be engaged with the fingers of a user's hand while the thumb of that hand is used to operate a firing tab 250.

Figure 18:
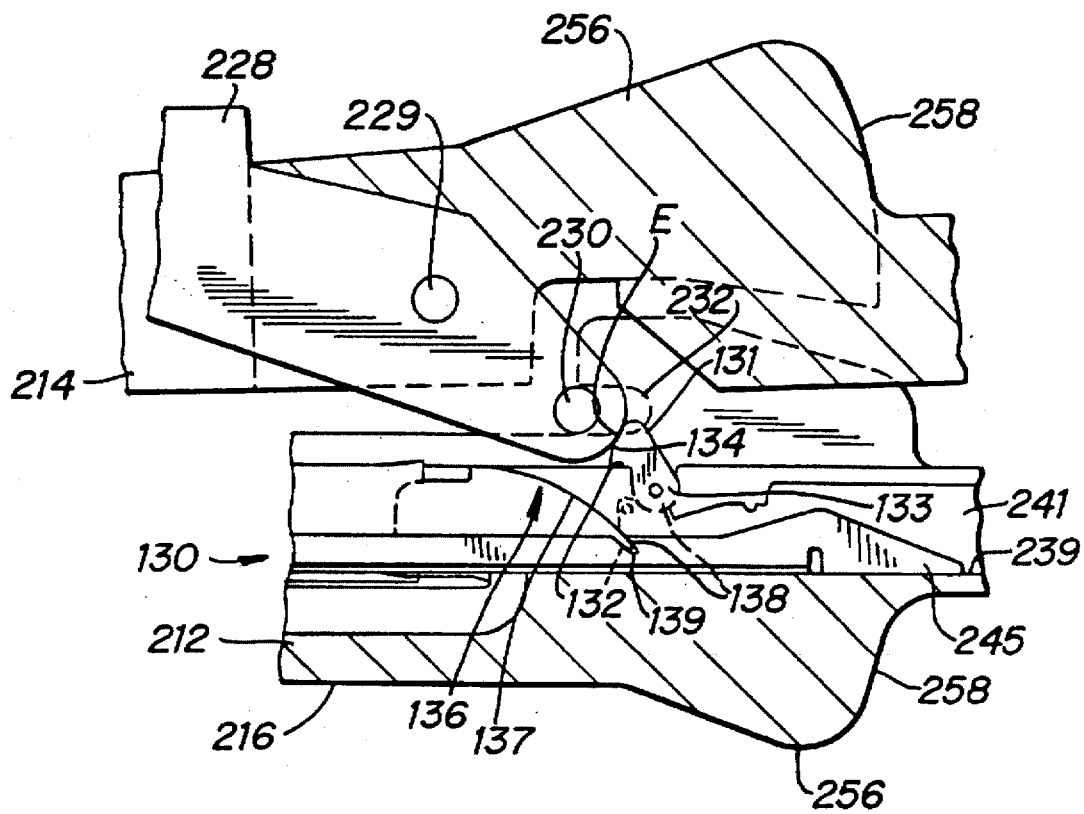
FIG. 18 is an enlarged sectional side view of the surgical stapling instrument of FIG. 16 and a fourth alternative embodiment of the cartridge assembly of the present invention.
Figure 19:
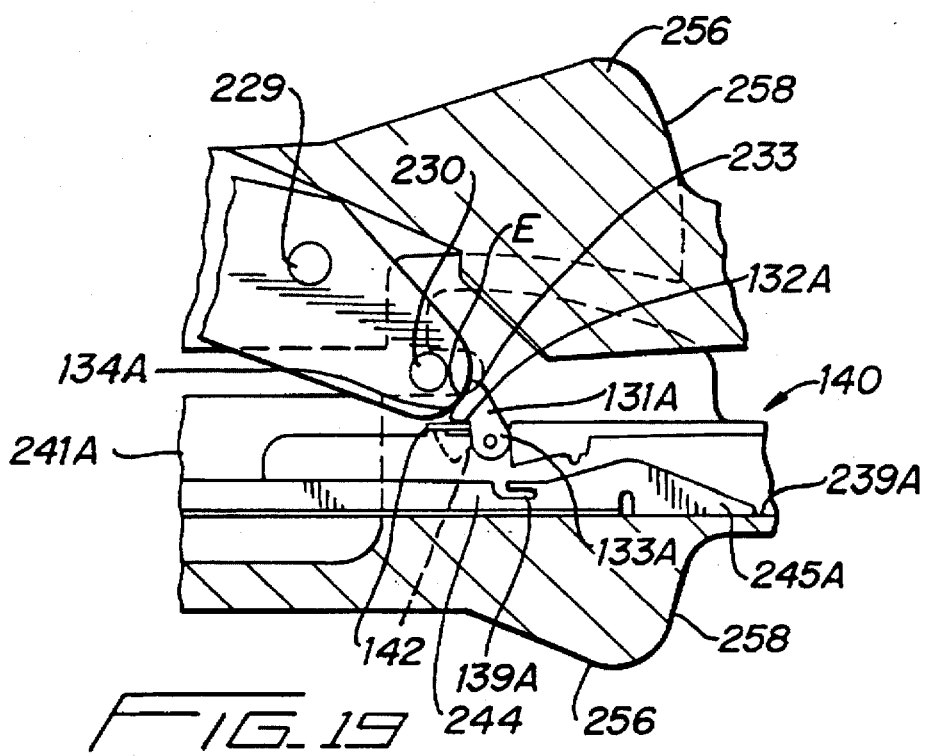
FIG. 19 is an enlarged sectional side view of the surgical stapling instrument of FIG. 16 and a fifth alternative embodiment of the cartridge assembly of the present invention.

A novel structure of the cartridge assembly 130 that distinguishes the present invention from "The ILA Stapler" stapling instrument/cartridge assembly combination of the prior art and which provides a safety feature which prevents the jaws 220, 222 of the stapler 200 from being approximated or clamped onto tissue when the stapler 200 is loaded with a spent stapler cartridge is shown in FIGS. 18 and 19.

FIG. 18 illustrates a fourth embodiment of cartridge assembly according to the present invention for use with the "ILA" type stapler 200 generally designated by the reference number 130. Like known stapler cartridges, the cartridge assembly 130 comprises an elongate fixed or removable anvil 240 positioned over and along the jaw part 222, and the jaw part 220 of the first structural member 212 has an elongate groove 239 adapted to receive a cartridge housing or body 241 of the cartridge assembly 130. The cartridge body 241 contains a plurality of staples 243 disposed in rows oriented longitudinally of the jaw part 220 in opposition to the anvil 240 when the structural members 212, 214 are in their closed position. Also, the cartridge assembly 130 includes a pair of manually actuatable means including cam-like drivers or pushers 245 fixed at one end of a drive rod 244 and adapted to be moved through longitudinal slots in the cartridge body 241 by manually pressing on a firing tab 250. The slots for the pushers 245 are offset from the middle portion of the cartridge body 241 to allow clearance for an optional knife. When the tab 250 is manually pressed, the drivers or pushers 245 sequentially eject the staples 243 from the cartridge body 241 by means of camming plungers 247 under the staples 243. The camming plungers 247 push the staples 243 toward a surface of the cartridge body 241 opposite the anvil 240 and thereby press the ejected staples 243 against specially shaped surfaces on the anvil 240 to engage and close the staples 243 in tissues between the jaw parts 220, 222 when the structural members 212, 214 are in their closed position.

Unlike known staple cartridges, the cartridge assembly 130 comprises one or more safety bodies 131 having first and second ends, shoulder surfaces 132, mounting surfaces 133 and abutment surfaces 134 located at the first end. The mounting surfaces 133 mount the first end of the safety body 131 on the cartridge housing 241 for pivotal movement of the safety body 132 between a pre-fired position (FIG. 18, dashed lines) for affording movement of the pin 230 of the elongate locking member 28 into full engagement with the U-shaped journal surfaces 232 of the first structural member 212 and a fired position (FIG. 18, solid lines) with the abutment surface 134 of the safety body 131 adapted to be positioned in engagement with a safety stop surface 233 located on the end E of the elongate locking member 228. The safety body 131 provides an impediment which prevents the pin 230 of the elongate locking member 228 from entering into full engagement with the U-shaped journal surfaces 232 of the first structural member 212 and thus prevents the jaws 220, 222 from being moved from the open to the closed position. Correspondingly, the safety body 131 prevents the cam surface 234 from engaging the cam (not shown) on the second structural member 214, and thereby prevents the locking member 228 from fully moving from its release to its locking position.

A means 136 is provided to drive the safety body 131 to the fired position in the form of a leaf spring 137. The leaf spring 137 has a distal end 138 which is initially in releasable engagement with a notch 139 in the pusher 245. The surfaces of the pusher 245 surrounding the notch 139 retain the leaf spring 137 in the pre-fired position when the pushers 245 are in the retracted position and release the leaf spring 137 to afford movement of the safety body 131 from the pre-fired to the fired positions when the pushers 245 are moved from the retracted to the extended position. Once the pushers 245 have been moved to the extended position, the distal end 138 of the leaf spring 137 is released and the distal end 138 of the leaf spring 137 then engages the shoulder surfaces 132 of the safety body 132 to drive the safety body 131 toward the fired position.

Like the safety arm 110, the safety body 131 will move to an intermediate position (not shown) between the pre-fired and fired positions. During movement of the pushers 245 from the retracted to the extended position, and while the first and second structural members 212, 214 remain in the closed position, the safety body 131 is not permitted to move completely to the fired position because it engages interfering surfaces on the elongate locking member 228. Once the first and second structural members 212, 214 are moved from the closed to the open positions, the safety body 131 will move under the influence of the leaf spring 137 to the fired position. Thereafter, any attempt to place the first and second structural members 212, 214 in the closed position while the first structural member 212 remains loaded with the spent cartridge will be thwarted since the abutment surface 134 will be in a position to contact the safety stop surface 233 and thereby prevents the pin 230 of the elongate locking member 28 from entering into full engagement with the U-shaped journal surfaces 232 of the first structural member 212.

The cartridge assembly 130 may comprise one safety body 131 or a plurality of safety bodies. For example, the cartridge assembly 130 could comprise two safety bodies 131 spaced laterally on opposite sides of the channel (not shown) for the optional blade. The safety body 131 or plurality of safety bodies should be offset from a middle portion of the cartridge body 241 to afford clearance for the optional blade or knife and its corresponding drive rod.

FIG. 19 illustrates a fifth embodiment of cartridge assembly according to the present invention generally designated by the reference numeral 140 which has many parts that are essentially the same as the parts of the cartridge assembly 130 and which have been identified by the same reference numeral to which the suffix "A" has been added. The main difference between the embodiment shown in FIGS. 18 and 19 is that the leaf spring 137 of FIG. 18 is replaced by the torsion spring 142. The function of the cartridge assembly 140 is otherwise identical to the function of the cartridge assembly 130.

The present invention has now been described with reference to several embodiments thereof. It will be apparent to those skilled in the art that many changes or additions can be made in the embodiments described without departing from the scope of the present invention. For example, the safety arm 110A may be mounted on the stapler 10 rather than the cartridge assembly 2. Also, the means for releasably retaining the safety member in the free-movement position and for releasing the safety member may comprise a release member mounted on the spring biased safety arm. The release member may be pivotally mounted on the safety member for movement between a locked position with the release member engaged with retention surfaces on the housing against the bias of the spring and a release position with the release member spaced from the retention surfaces. In this embodiment, the pushers may include bearing surfaces for actuating the safety member. Thus, the scope of the present invention should not be limited to the structures described in this application, but only by structures described by the language of the claims and the equivalents of those structures.

What is claimed is:

1. A staple cartridge assembly adapted for use in a surgical stapler having first and second structural members each being elongate in a first direction and each comprising a handle part having first and second ends and a jaw part projecting from said first end, said structural members having pivot means at said second ends adapted for free engagement and disengagement in a plane normal to said first direction for affording, when engaged, relative pivotal movement of said structural members between a closed position with said jaw parts in closely spaced relationship, and an open position with said jaw parts spaced farther from each other than in said closed position, said handle parts of said structural members in said closed position defining a space between said handle parts over the majority of the distance between said first and second ends when said structural members are in said closed position;

an elongate locking member having first and second ends, a safety stop surface adjacent the first end of the locking member, and a pivot point closely adjacent the first end of the locking member, the pivot point of said locking member being mounted on said second structural member adjacent the first end of said second structural member for pivotal movement between a locking position generally aligned with the handle part of said second structural member, and a release position with the second end of said locking member spaced from the second end of said second structural member, said first end of said locking member and said first end of said first structural member having surfaces adapted, when said pivot means are engaged with said structural members in said open position, for engagement during movement of said locking member from said release position to said locking position to forcefully move said structural members to said closed position, and means adapted for releasable engagement between said elongate locking member and said second structural member for holding said locking member in said locking position;

said first structural member being adapted to receive said staple cartridge assembly and said jaw part of said second structural member being adapted to receive an anvil;

wherein said staple cartridge assembly comprises:
a cartridge housing for enclosing a plurality of staples,
a pusher for sequentially pressing said plurality of staples within said cartridge housing against said anvil to engage and close the plurality of staples in tissues between said jaw parts when said structural members are in said closed position, said pusher being movable in said first direction between a retracted position with said plurality of staples enclosed within said cartridge housing and an extended position with said plurality of staples closed within tissue, manually actuatable means within said space between said handle parts for moving said pusher from said retracted to said extended position, and a safety body having first and second ends, said safety body having a shoulder surface between said first and second ends and an abutment surface generally adjacent said second end adapted to abut said safety stop surface, pivotal mounting means for mounting said first end of said safety body on said cartridge housing for pivotal movement of said safety body between a pre-fired position for affording movement of said structural members between said closed and open position and a fired position with said abutment surface of said safety body adapted to be in engagement with said safety stop surface, biasing means adapted to be received by said shoulder surface of said safety body for biasing said safety body toward said fired position, means for releasable engagement between said biasing means and said pusher for retaining said biasing means in a disengaged position when said pusher is in said retracted position and for releasing said biasing means to afford movement of said safety body toward said fired position under the influence of said biasing means when said pusher is moved from said retracted position toward said extended position, wherein after said pusher has been moved from said retracted position to said extended position, said biasing means has moved said safety body from said pre-fired position toward said fired position, and said first and second structural members are moved from said closed to said open position, said abutment surface will be in a position to prevent said first and second structural members from being moved to said closed position to thereby prevent accidental tissue trauma.

2. An apparatus for applying at least one row of surgical fasteners comprising:
a) a first cartridge section for receiving a cartridge containing at least two rows of fasteners and having a tissue contacting surface defining a first plane, the first cartridge section having a longitudinal axis;
b) a second anvil section for mating with the first cartridge section to clamp tissue therebetween;
c) an advancing mechanism including at least one cam bar for firing the fasteners and a knife bar for cutting tissue adjacent the rows of fasteners, the advancing mechanism being movable from a proximal position to a distal position to fire the fasteners; and
d) a pivotal latch member of generally elongate configuration mounted for movement with respect to the cartridge and being in an initial engaged position oriented transverse to the longitudinal axis of the cartridge section and spaced from a distal end thereof, the latch member being movable within a second plane about a single axis of rotation between said initial engaged position and a second disengaged position, wherein said second plane is perpendicular to said axis of rotation of the latch member and transverse to the first plane defined by the tissue contacting surface, and wherein movement of the advancing mechanism to a predetermined distance in a distal direction disengages the latch member for pivotal movement from the initial engaged position to the second disengaged position.

3. An apparatus as recited in claim 2, wherein the latch member is positioned proximal of a proximal-most fastener in the rows of fasteners.

4. An apparatus as recited in claim 3, wherein the blocking member includes retention surfaces for releasably engaging the latch member.

5. An apparatus as recited in claim 2, wherein the latch member retains a spring biased blocking member in a non-blocking position when said latch member is in said initial engaged position.

6. An apparatus as recited in claim 5, wherein the blocking member includes an abutment surface for engaging a safety stop surface defined on the anvil section.

7. An apparatus as recited in claim 5, said spring is a torsion spring which biases the blocking member toward a blocking position wherein the first cartridge section is blocked from mating with the second anvil section.

8. An apparatus as recited in claim 7, wherein the blocking member is mounted for rotation into the blocking position about an axis which extends perpendicular to the longitudinal axis of the cartridge section.

9. An apparatus as recited in claim 7, wherein the blocking member is mounted for rotation into the blocking position about an axis which extends perpendicular to the longitudinal axis of the cartridge section.

10. An apparatus as recited in claim 9, wherein the single pivot point about which the latch member is mounted to move defines an axis which is parallel to the axis about which the blocking member rotates.

11. An apparatus as recited in claim 9, wherein the single pivot point about which the latch member is mounted for rotation defines an axis which is parallel to the axis about which the blocking member rotates.

12. An apparatus for applying at least one row of surgical fasteners comprising:
a) a cartridge half section having a longitudinal axis and having a cartridge mounted therein, the cartridge containing a plurality of surgical fasteners arranged in at least one linear row and a tissue contacting surface defining a first plane;
b) an anvil half section including an anvil having a plurality of depressions to deform the surgical fasteners;
c) an advancing mechanism including a knife to cut tissue and a pair of cam bars slidable in a longitudinal direction to fire the fasteners in a direction transverse to the longitudinal axis; and
d) a lockout mechanism including a latch member mounted at a single pivot point to the cartridge, the latch member being rotatable within a second plane around an axis of rotation from a first position substantially transverse to the longitudinal axis to a second position, the second plane being perpendicular to the axis of rotation and transverse to the first plane, the latch member retaining a spring biased blocking member in a non-blocking position, wherein initial movement of the firing mechanism in a distal direction to fire the fasteners and cut tissue rotates the latch member to the second position, thereby allowing the blocking member to move toward the anvil half section into a blocking position.

13. An apparatus as recited in claim 12, wherein the latch member is positioned proximal of a proximal-most fastener in the linear row of fasteners.

14. An apparatus as recited in claim 12, wherein the latch member includes retention surfaces for releasably engaging the blocking member.

15. An apparatus as recited in claim 14, wherein the blocking member includes retention surfaces for releasably engaging the latch member.

16. An apparatus as recited in claim 12, wherein the blocking member includes an abutment surface for engaging a safety stop surface defined on the anvil section adjacent a proximal end of the anvil.

17. An apparatus as recited in claim 12, wherein a torsion spring biases the blocking member toward the blocking position wherein the first cartridge section is blocked from mating with the second anvil section.

18. An apparatus for applying surgical fasteners comprising:
   a) an elongated first jaw member having a distal channel portion configured to support a staple carrying cartridge which houses a plurality of surgical fasteners;
   b) an elongated second jaw member configured to support an anvil which defines a fastener forming surface against which fasteners ejected from the cartridge are driven, the first and second jaw members being configured to removably mate with one another in such a manner so that the cartridge and the anvil are arranged in close cooperative alignment;
   c) an actuation mechanism associated with a proximal portion of the first jaw member and mounted for movement through the cartridge in a longitudinal direction to sequentially eject surgical fasteners from the cartridge to be driven against the fastener forming surface of the anvil; and
   d) a blocking mechanism mounted for movement toward the second jaw member into a blocking position when the fasteners have been ejected and while the cartridge is disposed within the distal channel portion of the first jaw member, the blocking mechanism in the blocking position spanning a gap defined between the first and second jaw members to prevent subsequent arrangement of the cartridge and the anvil in close cooperative alignment.

19. An apparatus as recited in claim 18, further comprising biasing means for urging the blocking mechanism toward said blocking position.

20. An apparatus as recited in claim 18, further comprising retaining means for maintaining the blocking mechanism in a non-blocking position prior to moving the actuation mechanism through the cartridge to eject fasteners therefrom.

21. An apparatus as recited in claim 20, wherein the retaining means includes a latch member having retention surfaces for releasably engaging the blocking mechanism.

22. An apparatus as recited in claim 18, further comprising a cutting member operatively associated with the actuation mechanism and movable through the cartridge in conjunction therewith for incising tissue.

* * * * *